US008062870B2

(12) United States Patent
Gallop et al.

(10) Patent No.: US 8,062,870 B2
(45) Date of Patent: Nov. 22, 2011

(54) ENANTIOMERICALLY RESOLVING ACYLOXYALKYL THIOCARBONATES USED IN SYNTHESIZING ACYLOXYALKYL CARBAMATE PRODRUGS

(75) Inventors: Mark A. Gallop, Santa Clara, CA (US); Fenmei Yao, Mountain View, CA (US); Maria J. Ludwikow, Cupertino, CA (US); Ge Peng, Mountain View, CA (US); Stephen P. Raillard, Mountain View, CA (US)

(73) Assignee: XenoPort, Inc., Santa Clara, CA (US)

( * ) Notice: Subject to any disclaimer, the term of this patent is extended or adjusted under 35 U.S.C. 154(b) by 78 days.

(21) Appl. No.: 12/358,532

(22) Filed: Jan. 23, 2009

(65) Prior Publication Data
US 2009/0192325 A1 Jul. 30, 2009

Related U.S. Application Data

(60) Provisional application No. 61/023,808, filed on Jan. 25, 2008, provisional application No. 61/023,813, filed on Jan. 25, 2008, provisional application No. 61/121,859, filed on Dec. 11, 2008.

(51) Int. Cl.
C12P 11/00 (2006.01)
C12P 7/62 (2006.01)
C07C 329/06 (2006.01)
C07C 329/08 (2006.01)
C07C 329/10 (2006.01)

(52) U.S. Cl. ......... 435/129; 435/130; 435/135; 558/248

(58) Field of Classification Search .................. None
See application file for complete search history.

(56) References Cited

U.S. PATENT DOCUMENTS

| 4,024,175 | A | 5/1977 | Satzinger et al. |
| 4,126,684 | A | 11/1978 | Robson et al. |
| 4,760,057 | A | 7/1988 | Alexander |
| 4,916,230 | A | 4/1990 | Alexander |
| 5,006,560 | A | 4/1991 | Kreutner et al. |
| 5,563,175 | A | 10/1996 | Silverman et al. |
| 5,684,018 | A | 11/1997 | Alexander |
| 5,719,185 | A | 2/1998 | Bountra et al. |
| 6,020,370 | A | 2/2000 | Horwell et al. |
| 6,028,214 | A | 2/2000 | Silverman et al. |
| 6,103,932 | A | 8/2000 | Horwell et al. |
| 6,117,906 | A | 9/2000 | Silverman et al. |
| 6,117,908 | A | 9/2000 | Andrews et al. |
| 6,562,865 | B1 | 5/2003 | Codd et al. |
| 6,818,787 | B2 | 11/2004 | Gallop et al. |
| 6,927,036 | B2 | 8/2005 | Gallop et al. |
| 6,972,341 | B2 | 12/2005 | Gallop et al. |
| 7,026,351 | B2 | 4/2006 | Gallop et al. |
| 7,109,239 | B2 | 9/2006 | Gallop et al. |
| 7,186,855 | B2 | 3/2007 | Gallop et al. |
| 7,227,028 | B2 * | 6/2007 | Gallop et al. .......... 548/542 |
| 7,232,924 | B2 | 6/2007 | Raillard et al. |
| 7,300,956 | B2 | 11/2007 | Gallop et al. |
| 2004/0176456 | A1 | 9/2004 | Taylor et al. |
| 2004/0254246 | A1 | 12/2004 | Barrett et al. |
| 2005/0070483 | A1 | 3/2005 | Donevan et al. |
| 2005/0090550 | A1 | 4/2005 | Barrett |
| 2005/0192353 | A1 | 9/2005 | Barrett et al. |
| 2008/0161393 | A1 | 7/2008 | Barrett et al. |
| 2009/0118365 | A1 | 5/2009 | Benson, III et al. |
| 2009/0192222 | A1 * | 7/2009 | Yao et al. .................. 514/533 |

FOREIGN PATENT DOCUMENTS

| GB | 2 374 595 | 10/2002 |
| WO | WO 92/09560 | 6/1992 |
| WO | WO 93/23383 | 11/1993 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08670 | 2/1999 |
| WO | WO 99/08671 | 2/1999 |
| WO | WO 99/21824 | 5/1999 |
| WO | WO 99/31057 | 6/1999 |
| WO | WO 99/31074 | 6/1999 |
| WO | WO 99/31075 | 6/1999 |
| WO | WO 99/61424 | 12/1999 |
| WO | WO 00/15611 | 3/2000 |
| WO | WO 00/31020 | 3/2000 |
| WO | WO 00/50027 | 8/2000 |
| WO | WO 00/61135 | 10/2000 |
| WO | WO 01/08675 | 2/2001 |
| WO | WO 01/13904 | 3/2001 |
| WO | WO 01/26638 | 4/2001 |
| WO | WO 02/00209 | 1/2002 |
| WO | WO 02/096404 | 12/2002 |
| WO | WO 02/100347 | 12/2002 |
| WO | WO 2005/010011 | 2/2005 |
| WO | WO 2005/025563 | 3/2005 |
| WO | WO 2007/027476 | 3/2007 |
| WO | WO 2007/027477 | 3/2007 |
| WO | WO 2007/052999 | 5/2007 |

OTHER PUBLICATIONS

Chica et al. (Curr Opin Biotechnol. Aug. 2005;16(4):378-84.* U.S. Appl. No. 61/023,808, filed Jan. 25, 2008, Yao et al.
U.S. Appl. No. 61/023,813, filed Jan. 25, 2008, Yao et al.
U.S. Appl. No. 61/121,859, filed Dec. 11, 2008, Gallop et al.
Alexander et al., (Acyloxy)alkyl carbamate prodrugs of norfloxacin. *J. Med. Chem.* 1991, 34(1), 78-81.
Alexander et al., (Acyloxy)alkyl carbamates as novel bioreversible prodrugs for amines: increased permeation through biological membranes. *J. Med. Chem.* 1988, 31(2), 318-322.
Becker et al., Pregabalin is effective against behavioural and electrographic seizures during alcohol withdrawal. *Alcohol & Alcoholism* 2006, 41(4), 399-406.
Ben-David et al., Gabapentin therapy for vulvodynia. *Anesth, Analg.* 1999, 89, 1459-60.
Blommel and Blommel, Pregabalin: an antiepileptic agent useful for neuropathic pain. *Am J Health Syst Pharm* 2007, 64(14), 1475-82.
Bowsher, Neurogenic pain syndromes and their management. *Br. Med. Bull.* 1991, 47(3), 644-66.
Bryans et al., 3-Substituted GABA analogs with central nervous system activity: a review. *Med. Res. Rev.* 1999, 19(2), 149-177.

(Continued)

*Primary Examiner* — Rebecca Anderson
*Assistant Examiner* — Alicia L Otton
(74) *Attorney, Agent, or Firm* — Dorsey & Whitney LLP

(57) ABSTRACT

Methods of enzymatically resolving acyloxyalkyl thiocarbonates useful in the synthesis of acyloxyalkyl carbamate prodrugs are disclosed.

16 Claims, 5 Drawing Sheets

OTHER PUBLICATIONS

Bryans et al., Identification of novel ligands for the gabapentin binding site on the α2δ subunit of a calcium channel and their evaluation as anticonvulsant agents. *J. Med. Chem.* 1998, 41, 1838-1845.

Buvanendran et al., Preoperative cyclooxygenase-2 inhibitor treatment reduces the incidence of heterotopic ossification after hip arthroplasty: six-month follow-up. *Anesthesiology* 2007, 107(2), 358-359.

Ciccaglione and Marzio, Effect of acute and chronic administration of the $GABA_B$ agonist baclofen on 24 hour pH metry and symptoms in control subjects and in patients with gastro-esophageal reflux disease. *Gut* 2003, 52, 464-70.

Codd et al., Tramadol and several anticonvulsants synergize in attenuating nerve injury-induced allodynia. *Pain* 2008, 134, 254-262.

Coluzzi and Mattia, Chronic non-cancer pain: focus on once-daily tramadol formulations. *Ther Clin Risk Manage* 2007, 3(5), 819-29.

Crofford et al., Pregabalin for the treatment of fibromyalgia syndrome: results of a randomized, double-blind, placebo-controlled trial. *Arthritis and Rheumatism* 2005, 52(4), 1264-73.

Dahl et al., Protective premedication: an option with gabapentin and related drugs? A review of gabapentin and pregabalin in the treatment of post-operative pain. *Acta Anesthesiol Scand* 2004, 48(8), 1130-36.

Dapas et al., Baclofen for the treatment of acute low-back syndrome—a double-blind comparison with placebo. *Spine* 1985, 10(4), 345-9.

Freedman and O'Hara, Pregabalin has opioid-sparing effects following augmentation mamaplasty. *Aesthetic Surgery J* 2008, 28(4), 421-424.

Freitag, Preventative treatment for migraine and tension-type headaches: do drugs having effects on muscle spasm and tone have a role? *CNS Drugs* 2003, 17(6), 373-81.

Freynhagen et al., Efficacy of pregabalin in neuropathic pain evaluated in a 12-week, randomized, double-blind, multicentre, placebo-controlled trial of flexible- and fixed-dose regimens. *Pain* 2005, 115(3), 254-63.

Fromm et al., Role of inhibitory mechanisms in trigeminal neuralgia. *Neurology* 1981, 31, 683-7.

Gatti et al., Controlled-release oxycodone and pregabalin in the treatment of neuropathic pain: results of a multicenter Italian study. *Eur Neurol* 2009, 61, 129-137.

Gilron, Gabapentin and pregabalin for chronic neuropathic and early postsurgical pain: current evidence and future directions. *Curr Opin Anaesthesiol* 2007, 20, 456-472.

Gogate et al., N-(Acyloxyalkoxycarbonyl) derivatives as potential prodrugs of amines. I. Kinetics and mechanism of degradationin aqueous solutions. *International Journal of Pharmaceutics* 1987, 40, 235-248.

Grond and Sablotzky, Clinical pharmacology of tramadol. *Clin Pharmacokinet* 2004, 43(13), 879-923.

Guttuso et al., Gabapentin's effects on hot flashes in postmenopausal women: a randomized controlled trial. *Obstet. Gynecol.* 2003, 101(2), 337-345.

Guttuso, Gabapentin's effects on hot flashes and hypothermia. *Neurology* 2000, 54, 2161-2163.

Hanna et al., Prolonged-release oxycodone enhances the effects of existing gabapentin therapy in painful diabetic neuropathy patients. *Eur J Pain* 2008, 12, 804-13.

Heiss and Gais, Polyethylene glycol monomethyl ether-modified pig liver esterase: preparation, characterization and catalysis of enantioselective hydrolysis in water and acylation in organic solvents. *Tetrahedron Lett.* 1995, 36(22), 3833-3836.

Hill et al., Pregabalin in patients with postoperative dental pain. *Eur J Pain* 2001, 5, 119-124.

Hindmarch et al., A double-blind study in healthy volunteers to assess the effects on sleep of pregabalin compared with alprazolam and placebo. *Sleep* 2005, 28(2), 187-93.

Jeffery et al., Gabapentin for hot flashes in prostate cancer. *Ann. Pharmacother.* 2002, 36(3), 433-436.

Jokela et al., A randomized controlled trial of perioperative administration of pregabalin for pain after laparoscopic hysterectomy. *Pain* 2008, 134, 106-112.

Keskinbora et al., Gabapentin and an opioid combination versus opioid alone for the management of neuropathic cancer pain: a randomized open trial. *J Pain Symptom Manage* 2007, 34, 183-189.

Loprinzi et al., Pilot evaluation of gabapentin for treating hot flashes. *Mayo Clin. Proc.* 2002, 77, 1159-1163.

Mathew et al., Efficacy of gabapentin in migraine prophylaxis. *Headache* 2001, 41, 119-128.

Pande et al., Efficacy of the novel anxiolytic pregabalin in social anxiety disorder: a placebo-controlled, multicenter study. *J Clin Psychopharmacol* 2004, 24(2), 141-149.

Pohl et al., Efficacy of pregabalin in the treatment of generalized anxiety disorder: double-blind, placebo-controlled comparison of BID versus TID dosing. *J Clin Psychopharmacol* 2005, 25(2), 151-8.

Price et al., Are baclofen-sensitive $GABA_B$ receptors present on primary afferent terminals of the spinal cord? *Nature* 1984, 307, 71-4.

Rao et al., Efficacy of gabapentin in the management of chemotherapy-induced peripheral neuropathy: a phase 3 randomized, double-blind, placebo-controlled, crossover trial (N00C3). *Cancer* 2007, 110(9), 2110-8.

Raphael et al., Efficacy and adverse effects of intravenous lignocaine therapy in fibromyalgia syndrome. *BMC Musculoskeletal Disorders* 2002, 3(17), Epub Jun. 20, 2002 (8 pages).

Reuben et al., Preventing the development of chronic pain after orthopedic surgery with preventative multimodal analgesic techniques. *J Bone Joint Sur Am.* 2007, 89, 1343-1358.

Reuben et al., The analgesic efficacy of celecoxib, pregabalin, and their combination for spinal fusion surgery. *Anesth Analg.* 2006, 103(5), 1271-7.

Rickels et al., Pregabalin for treatment of generalized anxiety disorder: a 4-week, multicenter, double-blind, placebo-controlled trial of pregabalin and alprazolam. *Arch Gen Psychiatry* 2005, 62(9), 1022-1030.

Ringel and Roy, Glossopharyngeal neuralgia: successful treatment with baclofen. *Ann Neurol* 1987, 21(5), 514-5.

Ruoff et al., Tramadol/acetaminophen combination tablets for the treatment of chronic lower back pain: a multicenter, randomized, double-blind, placebo-controlled outpatient study. *Clinical Ther* 2003, 25(4), 1123-1141.

Ruppert and Gais, Activity enhancement of pig liver esterase in organic solvents by colyophilization with methoxypolyethylene glycol: kinetic resolution of alcohols. *Tetrahedron Asymmetry*, 1997, 8(21), 3657-3664.

Sabatowski et al., Pregabalin reduces pain and improves sleep and mood disturbances in patients with post-herpetic neuralgia: results of a randomized, placebo-controlled clinical trial. *Pain* 2004, 109, 26-35.

Saif and Hashmi, Successful amelioration of oxaliplatin-induced hyperexcitability syndrome with the antiepileptic pregabalin in a patient with pancreatic cancer. *Cancer Chemother Pharmacol* 2008, 61(3), 349-354.

Siddall et al., Pregabalin in central neuropathic pain associated with spinal cord injury: a placebo-controlled trial. *Neurology* 2006, 67(10), 1792-800.

Sommer et al., Pregabalin in restless legs syndrome with and without neuropathic pain. *Acta Neurol Scand* 2007, 115(5), 347-50.

Sun et al.; N-Acyloxymethyl carbamate linked prodrugs of pseudomycins are novel antifungal agents. *Bioorganic & Medicinal Chemistry Letters* 2001, 11, 1875-1879.

Taylor et al., Pharmacology and mechanism of action of pregabalin: the calcium channel α2-δ subunit as a target for antiepileptic drug discovery. *Epilepsy Res* 2007, 73(2), 137-50.

Tiippana et al., Do surgical patients benefit from perioperative gabapentin/pregabalin? A systematic review of efficacy and safety. *Anesth Analg* 2007, 104, 1545-56.

Tzschentke et al., (−)-(1R,2R)-3-(3-Dimethylamino-1-ethyl-2-methyl-propyl)-phenol hydrochloride (Tapentadol HCl): a novel μ-opioid receptor agonist/norepinephrine reuptake inhibitor with broad-spectrum analgesic properties. *J Pharm Expt'l Ther* 2007, 323(1), 265-276.

van Herwaarden et al., The effect of baclofen on gastro-esophageal reflux, lower esophageal sphincter function and reflux symptoms in patients with reflux disease. *Aliment. Pharmacol. Ther.* 2002, 16, 1655-62.

Wessely et al., Preliminary results of a double blind study with the new migraine prophylactic drug gabapentin. *Cephalalgia* 1987, 7(Suppl 6), 477-478).

Woolf and Chong, Preemptive analgesia—treating postoperative pain by preventing the establishment of central sensitization. *Anesth Analg* 1993, 77(2), 362-79.

Zareba, Pregabalin: a new agent for the treatment of neuropathic pain. *Drugs Today* 2005, 41(8), 509-16.

Zuniga et al., Intrathecal baclofen is analgesic in patients with chronic pain. *Anesthesiology* 2000, 92(3), 876-880.

Bornscheuer, et al., "Hydrolases in Organic Synthesis. Regio- and Stereoselective Biotransformations. 2nd Edition.", Wiley-VCH (2005), p. 61-183.

International Search Report, dated Aug. 19, 2009, issued in PCT Application No. PCT/US2009/031873 (5 pages).

Written Opinion of the International Searching Authority, dated Aug. 19, 2009, issued in PCT Application No. PCT/US2009/031873 (10 pages).

\* cited by examiner

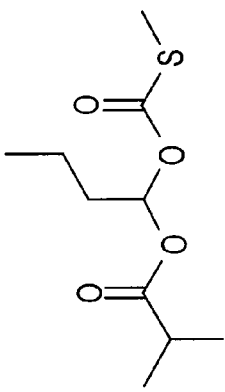
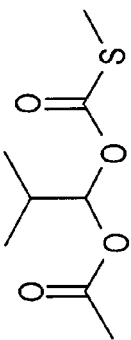
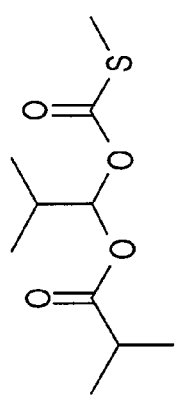
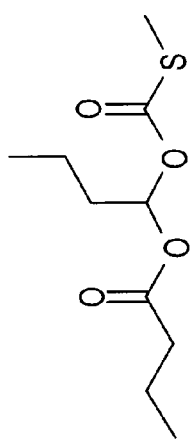
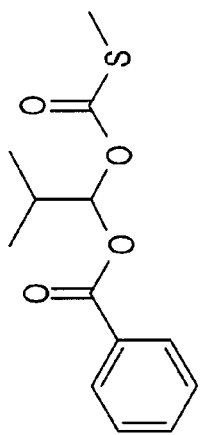
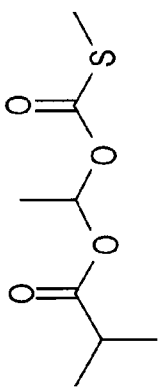
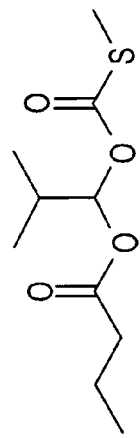
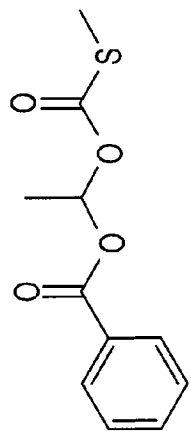
FIG.3

| COMPOUND | R¹ | R² | PROCINE LIVER ESTERASE | CANDIDA RUGOSA LIPASE | CANDIDA CYLINDRACEA LIPASE | CANDIDA ANTARCTICA LIPASE B | CANDIDA ANTARCTICA LIPASE A |
|---|---|---|---|---|---|---|---|
| 2A | ISOPROPYL | METHYL | NOT SELECTIVE | R | R | R | – |
| 2B | ISOPROPYL | ISOPROPYL | S | R | R | NOT SELECTIVE | S |
| 2C | ISOPROPYL | N-PROPYL | S | R | R | NOT SELECTIVITY | – |
| 2D | N-PROPYL | ISOPROPYL | S | NOT SELECTIVE | NOT SELECTIVE | R | – |
| 2E | N-PROPYL | N-PROPYL | S | R | R | NOT SELECTIVE | – |
| 2F | METHYL | ISOPROPYL | S | R | R | R | – |
| 2G | PHENYL | METHYL | NOT SELECTIVE | R | – | S | – |
| 2H | PHENYL | ISOPROPYL | NOT SELECTIVE | R | – | NOT SELECTIVE | – |

– NOT DETERMINED

FIG.4

ENANTIOMERICALLY RESOLVING ACYLOXYALKYL THIOCARBONATES USED IN SYNTHESIZING ACYLOXYALKYL CARBAMATE PRODRUGS

This application claims the benefit under 35 U.S.C. §119 (e) of U.S. Provisional Application Ser. Nos. 61/023,808 filed Jan. 25, 2008; 61/023,813 filed Jan. 25, 2008; and 61/121,859 filed Dec. 11, 2008, each of which is incorporated by reference in its entirety.

FIELD

Methods provided by the present disclosure relate to the enzymatic resolution of acyloxyalkyl thiocarbonates useful in the synthesis of acyloxyalkyl carbamate prodrugs.

BACKGROUND

The oral bioavailability of certain drugs can be improved by conversion to prodrugs. Certain prodrugs are derivatives of the parent drug in which a functional group is "masked" by a promoiety. Following administration to a patient the prodrug is metabolized to release the parent drug. The 1-(acyloxy)-alkyl group is an example of a promoiety that has been used to functionalize amine-containing drugs such as pregabalin and baclofen.

Pregabalin ((3S)-(aminomethyl)-5-methyl-hexanoic acid) is an FDA approved drug that is marketed for the treatment of, for example, post herpetic neuralgia, peripheral diabetic neuropathy, fibromyalgia, and epilepsy. Pregabalin is not absorbed from the lower gastrointestinal tract and exhibits a short half life in vivo, and therefore frequent dosing is required to maintain therapeutic levels in the body when orally administered. (3S)-{[1-Isobutanoyloxyethoxy]carbonylaminomethyl}-5-methyl-hexanoic acid, (3S)-{[1-isobutanoyloxyisobutoxy]carbonylaminomethyl}-5-methyl-hexanoic acid, and (3S)-{[1-benzoyloxyethoxy]carbonylaminomethyl}-5-methyl-hexanoic acid are examples of 1-(acyloxy)-alkyl carbamate prodrugs of pregabalin, which exhibit high bioavailability as pregabalin when dosed either orally or directly into the colon of a mammal (Gallop et al., U.S. Pat. Nos. 6,972,341 and 7,186,855; and Yao and Gallop, U.S. Provisional Application Nos. 61/023,808 filed Jan. 25, 2008 and 61/023,813 filed Jan. 25, 2008, each of which is incorporated by reference in its entirety).

The 1-(acyloxy)-alkyl promoiety has also been used to provide prodrugs of baclofen, (±)-4-amino-3-(4-chlorophenyl)butanoic acid. Gallop et al., U.S. Pat. No. 7,109,239 and U.S. Pat. No. 7,300,956 (each of which is incorporated by reference in its entirety) disclose 1-(acyloxy)-alkyl carbamate prodrugs of R-baclofen such as (3R)-4-{[(1S)-2-methyl-1-(2-methylpropanoyloxy)propoxy]carbonylamino}-3-(4-chlorophenyl)butanoic acid. Baclofen is an analog of gamma-aminobutyric acid (GABA) that selectively activates $GABA_B$ receptors, resulting in neuronal hyperpolarization. Baclofen is an FDA approved drug that is marketed for the treatment of spasticity and muscle relaxation. More recent studies have indicated that the R-isomer of baclofen is effective for treating gastroesophageal reflux disease (GERD). Baclofen and R-baclofen, like pregabalin, have poor colonic absorption and a short half life in vivo, and when orally administered frequent dosing is required to maintain therapeutic levels in the body.

The (acyloxy)alkylcarbamate functionality has been widely used to prepare prodrugs for therapeutics containing amine groups (Gogate et al., International Journal of Pharmaceutics 1987, 40, 235-248; Alexander et al., J. Med. Chem. 1988, 31, 318-322; Sun et al., Bioorganic & Medicinal Chemistry Letters 2001, 11, 1875-1879; Alexander et al., J. Med. Chem. 1991, 34, 78-81; and Gallop et al., U.S. Pat. No. 6,972,341). Methods of synthesizing 1-(acyloxy)-alkyl carbamate prodrugs are disclosed in Gallop et al., U.S. Pat. Nos. 6,818,787, 6,927,036, 6,972,341, 7,186,855, 7,026,351, 7,109,239, and 7,227,028; Raillard et al., U.S. Pat. No. 7,232,924; Gallop and Bhat, WO 2005/010011; Raillard et al., U.S. Provisional Application No. 61/087,056 filed Aug. 7, 2008 and 61/087,038 filed Aug. 7, 2008, each of which is incorporated by reference in its entirety); and in Alexander, U.S. Pat. Nos. 4,760,057, 4,916,230, and 5,684,018. One method, as outlined in FIG. 1, involves an acyloxyalkylthiocarbonate intermediate (Sun et al., Bioorganic & Medicinal Chemistry Letters 2001, 11, 1875-1879; and Gallop et al., U.S. Pat. Nos. 7,026,351 and 7,227,028).

A deficiency common to such methods for synthesizing acyloxyalkyl derivatives is that, except when the $R^2$ substituent is hydrogen, the prodrugs are generated as racemates or diastereomeric mixtures. The presence of an additional chiral center in the promoiety may lead to differences in the physical properties and in the pharmacokinetics of the prodrug. Complexities associated with the introduction of an uncontrolled stereocenter in acyloxyalkyl promoieties have led others to focus prodrug design efforts around the achiral acyloxymethyl moiety ($R^2$ is hydrogen). Further, many (acyloxy)alkylcarbamate prodrugs generate formaldehyde as a toxic metabolite during hydrolysis in vivo. In comparison with acetaldehyde, formaldehyde shows greater acute mammalian toxicity and mutagenicity, and its oxidative metabolite formate is associated with specific ocular toxicity in humans. Furthermore, because the thiocarbonates do not have acidic or basic functional groups, they are not readily resolved by classical chemical methods.

Thus, improved methods of synthesizing enantiomerically enriched acyloxyalkyl thiocarbonates are desirable.

SUMMARY

Methods of enzymatically resolving racemic acyloxyalkyl thiocarbonate intermediates useful in the synthesis of enantiomerically and diastereomerically enriched acyloxyalkyl carbamate prodrugs are disclosed. The methods are applied to the synthesis of acyloxyalkyl carbamate prodrugs of pregabalin and baclofen e.g., (3S)-{[(1R)-isobutanoyloxyethoxy]carbonylaminomethyl}-5-methyl-hexanoic acid and (3R)-4-{[(1S)-2-methyl-1-(2-methylpropanoyloxy)propoxy]carbonylamino}-3-(4-chlorophenyl)butanoic acid, respectively, with high chemical yield and diasteromeric excess.

In a first aspect, methods of enzymatically enriching an enantiomeric mixture of a compound of Formula (I) are disclosed comprising:

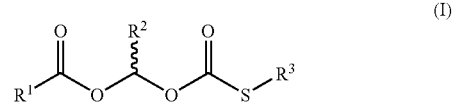

(I)

reacting the enantiomeric mixture with an enzyme to provide an enantiomerically enriched mixture having at least 90% enantiomeric excess of one enantiomer of the compound of Formula (I), wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl.

In a second aspect, an enantiomerically enriched mixture of a compound of Formula (I) is disclosed, the mixture having at least 90% enantiomeric excess of one enantiomer of the compound of Formula (I),

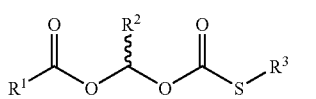
(I)

wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl is disclosed. The enantiomerically enriched mixture is prepared by steps comprising reacting an enantiomeric mixture of the compound of Formula (I) with an enzyme to provide the enantiomerically enriched mixture.

In a third aspect, methods of synthesizing an enantiomerically enriched mixture of an NHS-acyloxyalkylcarbonate compound of Formula (II) are disclosed comprising:

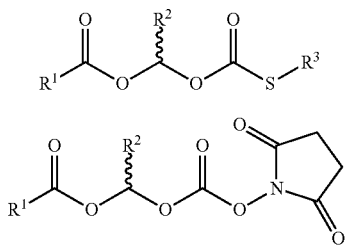

reacting an enantiomeric mixture of a compound of Formula (I) with an enzyme to provide an enantiomerically enriched mixture having at least 90% enantiomeric excess of one isomer of the compound of Formula (I), wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl; and reacting the enantiomerically enriched mixture having at least 90% enantiomeric excess of one enantiomer of the compound of Formula (I) with N-hydroxysuccinimide to provide the enantiomerically enriched mixture of the corresponding compound of Formula (II).

In a fourth aspect, methods of synthesizing an acyloxyalkyl carbamate prodrug of Formula (III) are disclosed, comprising:

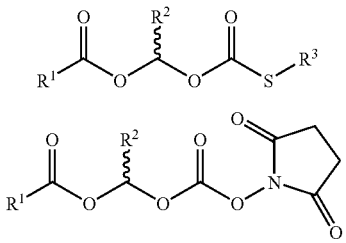

reacting an enantiomeric mixture of a compound of Formula (I) with an enzyme to provide an enantiomerically enriched mixture having at least 90% enantiomeric excess of one isomer of the compound of Formula (I), wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl;

reacting the enantiomerically enriched mixture with N-hydroxysuccinimide to provide the enantiomerically enriched mixture of the corresponding compound of Formula (II); and reacting the enantiomerically enriched compound of Formula (II) with a drug, D-NHR$^4$, comprising at least one primary or secondary amine group to provide the compound of Formula (III), wherein -D is the drug without the at least one primary or secondary amine group and $R^4$ is chosen from hydrogen and a group of a secondary amine.

BRIEF DESCRIPTION OF THE DRAWINGS

FIG. 3 shows the structure of certain racemic acyloxyalkyl thiocarbonates.

FIG. 4 shows a summary of the enantiomeric selectivity of certain enzymes towards acyloxyalkyl thiocarbonates.

DETAILED DESCRIPTION

Definitions

Figure 1:
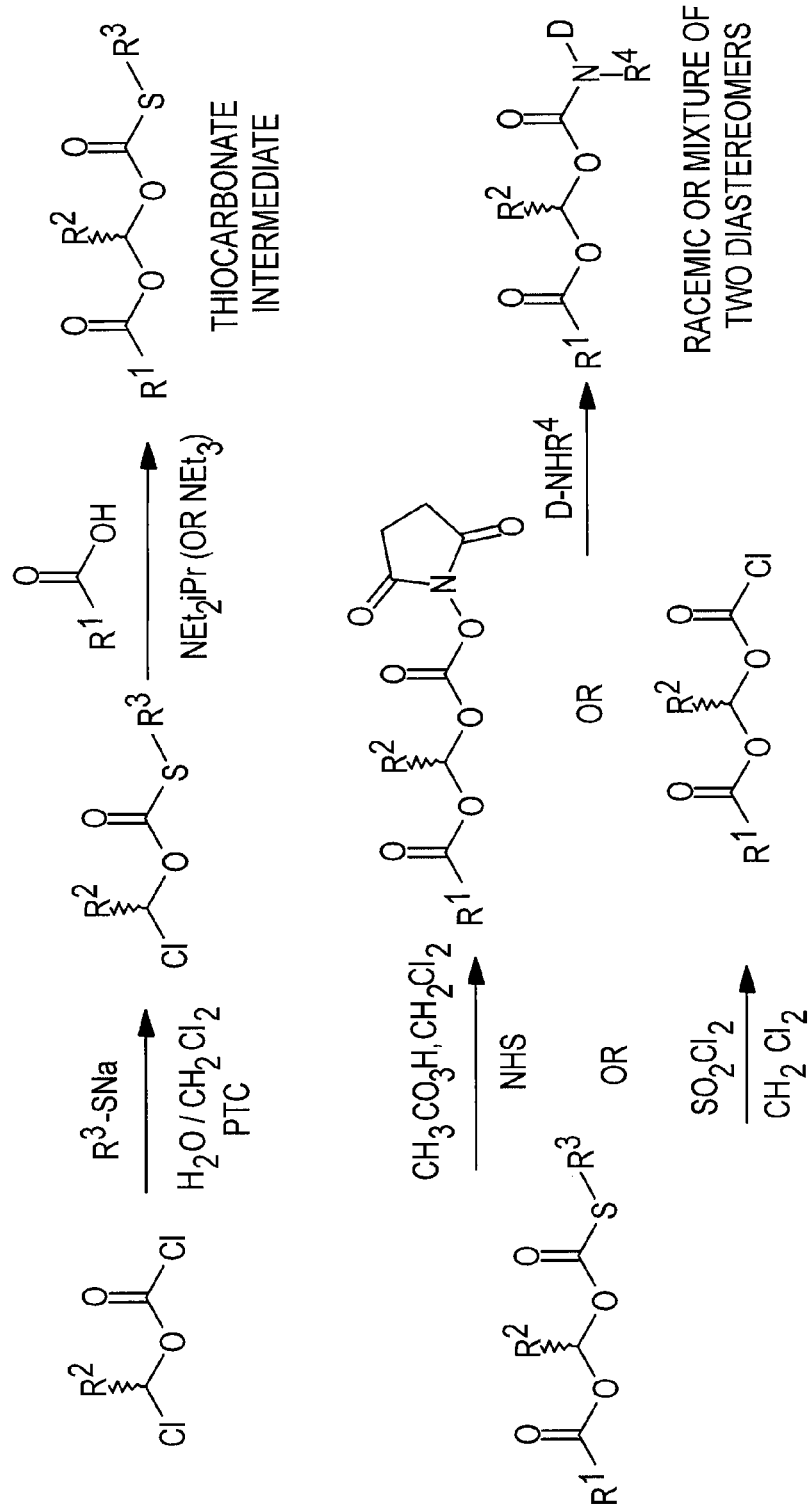
FIG. 1 shows a reaction sequence for the synthesis of acyloxyalkyl carbamate prodrugs via racemic acyloxyalkyl thiocarbonate intermediates.

A dash ("-") that is not between two letters or symbols is used to indicate a point of attachment for a moiety or substituent. For example, —CONH$_2$ is bonded through the carbon atom.

A waved dash ("⁓") between two letters or symbols is used to indicate a point of attachment for a moiety or substituent and a chiral center at which two enantiomers can be formed. The two enantiomers can be in equimolar quantities (forming a "racemate"), or a first enantiomer can be in excess of the second enantiomer (forming an "enantiomeric excess" or "enantiomeric mixture").

"Alkyl" by itself or as part of another substituent refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Alkoxycarbonyl" by itself or as part of another substituent refers to a radical —C(O)OR$^{31}$ where R$^{31}$ represents an alkyl or cycloalkyl group as defined herein. Examples of alkoxycarbonyl groups include methoxycarbonyl, ethoxycarbonyl, propoxycarbonyl, butoxycarbonyl, cyclohexyloxycarbonyl, and the like.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), and in certain embodiments, from 6 to 10 carbon atoms ($C_{6-10}$). Aryl, however, does not encompass or overlap in any way with heteroaryl, separately defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$.

"Compounds" of the present disclosure include any specific compounds within these formulae. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, unless specifically indicated, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. For example, resolution of the enantiomers or diasteriomers may be accomplished, for example, by conventional methods such as crystallization in the presence of a resolving agent, or chromatography, using, for example a chiral high-pressure liquid chromatography (HPLC) column.

Compounds of the present disclosure may also exist in several tautomeric forms including the enol form, the keto form, and mixtures thereof. Accordingly, the chemical structures depicted herein encompass all possible tautomeric forms of the illustrated compounds. Compounds of the present disclosure also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated, or N-oxides. Certain compounds may exist in multiple crystalline, co-crystalline, or amorphous forms. Compounds of the present disclosure include pharmaceutically acceptable salts thereof, or pharmaceutically acceptable solvates of the free acid form of any of the foregoing, as well as crystalline forms of any of the foregoing.

Further, when partial structures of the compounds are illustrated, an asterisk (*) indicates the point of attachment of the partial structure to the rest of the molecule.

"Cycloalkoxycarbonyl," by itself or as part of another substituent, refers to the radical —C(O)OR$^{32}$ where R$^{32}$ represents an cycloalkyl group as defined herein. Examples of cycloalkoxycarbonyl groups include, but are not limited to, cyclobutyloxycarbonyl, cyclohexyloxycarbonyl, and the like.

"Cycloalkyl" by itself or as part of another substituent refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, $C_{3-8}$ cycloalkyl, and in certain embodiments, $C_{3-6}$ cycloalkyl.

"Diastereomer" refers to a stereoisomer other than an enantiomer. Diastereoisomers (or diastereomers) are stereoisomers not related as mirror images. Diastereoisomers are characterized by differences in physical properties, and by some differences in chemical behavior towards achiral as well as chiral agents.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ".

"Drug comprising at least one primary or secondary amine group" means a drug having a primary amine group of the structure D-NH$_2$ where —NH$_2$ is a primary amine group and D- is the remaining portion of the drug without the primary amine group; and/or a drug having a secondary amine group of the structure D-NHR' wherein —NHR' is a secondary amine group such that R' is a group other than hydrogen and D- is the remaining portion of the drug without the secondary amine group. Thus, a drug comprising at least one primary or secondary amine group has the structure D-NHR$^4$ wherein -D is the drug without the at least one primary or secondary amine group and R$^4$ is chosen from hydrogen and a group of a secondary amine.

"Enantiomer" refers to one of a pair of molecular entities, which are mirror images of each other and non-superposable.

"Enantiomeric excess" refers to the absolute value of the difference between the mole or weight fractions of the (+) and the (−) enantiomers in a mixture of the two enantiomers. The percent enantiomeric excess is the enantiomeric excess multiplied by 100. The enantiomeric excess is abbreviated as e.e.

"Enantiomeric mixture" refers to a mixture of a compound having an enantiomeric ratio greater than 50:50 but less than 100:0.

"Enantiomeric ratio" refers to the ratio of the percentage of one enantiomer in a mixture to that of the other enantiomer.

"Enantiomerically enriched" refers to a sample of a chiral substance in which the enantiomeric ratio is greater than 50:50 but less than 100:0. An enantiomerically enriched sample will have a non-zero enantiomeric excess.

"GABA analog" refers to a compound having the structure:

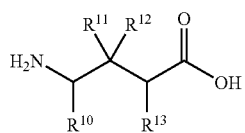

wherein:

R$^{10}$ and R$^{13}$ are independently chosen from hydrogen, $C_{1-6}$ alkyl, substituted $C_{1-6}$ alkyl, $C_{6-10}$ aryl, substituted $C_{6-10}$ aryl, $C_{7-16}$ arylalkyl, substituted $C_{7-16}$ arylalkyl, $C_{3-10}$ cycloalkyl, and substituted $C_{3-10}$ cycloalkyl;

R$^{11}$ and R$^{12}$ are independently chosen from hydrogen, $C_{1-6}$ alkyl, substituted $C_{1-6}$ alkyl, $C_{6-10}$ aryl, substituted $C_{6-10}$ aryl, $C_{7-16}$ arylalkyl, substituted $C_{7-16}$ arylalkyl, $C_{3-10}$ cycloalkyl, and substituted $C_{3-10}$ cycloalkyl; or R$^{11}$ and R$^{12}$ together with the carbon atom to which they are bonded form a $C_{3-10}$ cycloalkyl, substituted $C_{3-10}$ cycloalkyl, $C_{3-10}$ heterocycloalkyl, or substituted $C_{3-10}$ heterocycloalkyl ring.

In certain embodiments of a GABA analog, each substituent group is independently chosen from halogen, —NH$_2$, —OH, —CN, —COOH, —C(O)NH$_2$, —C(O)OR$^{14}$, and —NR$^{14}_3{}^+$ wherein each R$^{14}$ is independently $C_{1-3}$ alkyl.

In certain embodiments of a GABA analog, each of R$^{10}$ and R$^{13}$ is hydrogen. In certain embodiments of a GABA analog, R$^{11}$ is chosen from $C_{1-4}$ alkyl, substituted $C_{1-4}$ alkyl, $C_{1-4}$ alkoxycarbonyl, $C_{3-5}$ cycloalkyl, $C_{3-6}$ cycloalkoxycarbonyl, phenyl, substituted phenyl, and $C_{7-9}$ phenylalkyl; and R$^{12}$ is hydrogen. In certain embodiments of a GABA analog, each of R$^{10}$ and R$^{13}$ is hydrogen; R$^{11}$ is chosen from $C_{1-4}$ alkyl, substituted $C_{1-4}$ alkyl, $C_{1-4}$ alkoxycarbonyl, $C_{3-5}$ cycloalkyl, $C_{3-6}$ cycloalkoxycarbonyl, phenyl, substituted phenyl, and $C_{7-9}$ phenylalkyl; and R$^{12}$ is hydrogen.

In certain embodiments of a GABA analog, each of R$^{10}$, R$^{12}$, and R$^{13}$ is hydrogen; and R$^{11}$ is chosen from isobutyl and 4-chlorophenyl.

In certain embodiments, a GABA analog is chosen from pregabalin and baclofen. Furthermore, a number of GABA analogs with considerable pharmaceutical activity have been synthesized and are included within the scope of GABA analog (Satzinger et al., U.S. Pat. No. 4,024,175; Silverman et al, U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, WO 92/09560; Silverman et al., WO 93/23383; Horwell et al., WO 97/29101, Horwell et al., US WO 97/33858; Horwell et al., WO 97/33859; Bryans et al., WO 98/17627; Guglietta et al., WO 99/08671; Bryans et al., WO 99/21824; Bryans et al., 99/31057; Belliotti et al., WO 99/31074; Bryans et al., WO 99/31075; Bryans et al., WO 99/61424; Bryans et al., 00/15611; Bryans, WO 00/31020; Bryans et al., WO 00/50027; Bryans et al., WO 02/00209; Bryans et al., J. Med. Chem. 1998, 41, 1838-1845; Bryans et al., Med. Res. Rev. 1999, 19, 149-177, Guglietta et al., WO 99/08670; Bryans et al., WO 99/21824; Bryans et al., GB 2 374 595, Barta et al., U.S. 2003/0195251; and Donevan et al., 2005/0070483). Pharmaceutically important GABA analogs include, for example, gabapentin, pregabalin, vigabatrin, and baclofen.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heteroatom is chosen from O and N.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt can be in the form of a hydrate or other solvate. In certain embodiments, pharmaceutically acceptable addition salts include metal salts such as sodium, potassium, aluminum, calcium, magnesium and zinc salts, and ammonium salts such as isopropylamine, diethylamine, and diethanolamine salts. In certain embodiments, a pharmaceutically acceptable salt is the hydrochloride salt. In certain embodiments, a pharmaceutically acceptable salt is the sodium salt. Pharmaceutically acceptable salts may be prepared by the skilled chemist, by treating a compound of Formula (III) with an appropriate base in a suitable solvent, followed by crystallization and filtration.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a therapeutic agent may be administered to a patient and which does not destroy the pharmacological activity thereof and which is nontoxic when administered in doses sufficient to provide a therapeutically effective amount of the compound.

"Phenylalkyl" refers to an acyclic alkyl radical in which one of the hydrogen atoms bonded to a carbon atom, typically a terminal or sp$^3$ carbon atom, is replaced with a phenyl group. In certain embodiments, a phenylalkyl group is $C_{7-9}$ phenylalkyl in which the alkyl group is $C_{1-3}$ alkyl.

"Prodrug" refers to a derivative of a pharmaceutically active compound (drug) that undergoes a transformation under the conditions of use, such as within the body, to release the active drug. Prodrugs are frequently, but not necessarily, pharmacologically inactive until converted into the active drug. Prodrugs can be obtained by bonding a promoiety (defined herein), typically via a functional group, to a drug. For example, pregabalin prodrug (18) is metabolized within a patient's body to form the parent drug pregabalin.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Racemate" refers to an equimolar mixture of a pair of enantiomers.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules are water. In certain embodiments, compounds of the present disclosure and salts thereof may form solvates.

"Substituted" refers to a group in which one or more hydrogen atoms are independently replaced with the same or different substituent group(s). In certain embodiments, each substituent is independently chosen from halogen, —OH, —CN, —CF$_3$, =O, —NO$_2$, $C_{1-3}$ alkoxy, $C_{1-3}$ alkyl, —COOR$^{15}$ wherein R$^{15}$ is chosen from hydrogen and $C_{1-3}$ alkyl, and —N(R$^{15}$)$_2$ wherein each R$^{15}$ is independently chosen from hydrogen and $C_{1-3}$ alkyl. In certain embodiments, each substituent is independently chosen from halogen, —OH, —CN, —CF$_3$, —OCF$_3$, =O, —NO$_2$, $C_{1-6}$ alkoxy, $C_{1-6}$ alkyl, —COOR$^{15}$, —N(R$^{15}$)$_2$, and —CON(R$^{15}$)$_2$; wherein each R$^{15}$ is independently chosen from hydrogen and $C_{1-6}$ alkyl. In certain embodiments, each substituent is chosen from $C_{1-4}$ alkyl, —OH, and —NH$_2$.

"Sustained release" refers to release of a therapeutic or preventive amount of a drug or an active metabolite thereof over a period of time that is longer than that of a conventional formulation of the drug. For oral formulations, the term "sustained release" typically means release of the drug within the gastrointestinal tract lumen over a time period ranging, for example, from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of a conventional formulation of the drug.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. A "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

Reference is now made in detail to certain embodiments of compounds, compositions, and methods. The disclosed embodiments are not intended to be limiting of the claims. To the contrary, the claims are intended to cover all alternatives, modifications, and equivalents.

Methods of Enantiomeric Enrichment

Methods provided by the present disclosure include methods of enzymatically enriching an enantiomeric mixture of an acyloxyalkyl thiocarbonate of compound of Formula (I):

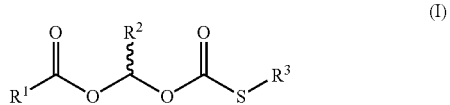

(I)

comprising the step of reacting the enantiomeric mixture with an enzyme to provide an enantiomerically resolved mixture having at least 90% enantiomeric excess of one enantiomer of the compound of Formula (I), wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl.

In certain embodiments of a compound of Formula (I), $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl. In certain embodiments of a compound of Formula (I), $R^1$ is chosen from methyl, ethyl, n-propyl, isopropyl, n-butyl, isobutyl, phenyl, and cyclohexyl. In certain embodiments of a compound of Formula (I), $R^1$ is chosen from methyl, n-propyl, isopropyl, and phenyl.

In certain embodiments of a compound of Formula (I), $R^2$ is chosen from methyl, ethyl, n-propyl, isopropyl, n-butyl, isobutyl, sec-butyl, phenyl, and cyclohexyl. In certain embodiments of a compound of Formula (I), $R^2$ is chosen from methyl, ethyl, n-propyl, and isopropyl. In certain embodiments of a compound of Formula (I), $R^2$ is chosen from methyl, n-propyl, and isopropyl.

In certain embodiments of a compound of Formula (I), $R^3$ is chosen from methyl, ethyl, n-propyl, isopropyl, n-butyl, isobutyl, sec-butyl, phenyl, and cyclohexyl. In certain embodiments of a compound of Formula (I), $R^3$ is chosen from methyl, ethyl, n-propyl, and isopropyl. In certain embodiments of a compound of Formula (I), $R^3$ is methyl.

In certain embodiments of a compound of Formula (I), $R^1$ is chosen from methyl, isopropyl, n-propyl, and phenyl; $R^2$ is chosen from methyl, isopropyl, and n-propyl; and $R^3$ is methyl.

In certain embodiments of a compound of Formula (I), each substituent is independently chosen from halogen, —OH, —CN, —CF$_3$, =O, —NO$_2$, $C_{1-3}$ alkoxy, $C_{1-3}$ alkyl, —COOR$^{15}$ wherein $R^{15}$ is chosen from hydrogen and $C_{1-3}$ alkyl, and —N(R$^{15}$)$_2$ wherein each $R^{15}$ is independently chosen from hydrogen and $C_{1-3}$ alkyl.

In certain embodiments, the enantiomerically resolved mixture has an enantiomeric excess of the R enantiomer and the enzyme is a lipase chosen from *Candida rugosa*, *Candida cylindracea*, and *Candida antarctica* lipase B.

In certain embodiments, the enantiomerically resolved mixture has an enantiomeric excess of the S enantiomer and the enzyme is a lipase chosen from porcine liver esterase, *Candida antarctica* lipase A, and *Candida antarctica* lipase B.

In certain embodiments, the enzyme is *Candida antarctica* lipase A, $R^1$ is isopropyl, $R^2$ is isopropyl, $R^3$ is methyl, and the enantiomerically resolved mixture has an enantiomeric excess of the S enantiomer of the compound of Formula (I).

In certain embodiments, the enzyme is *Candida antarctica* lipase B, $R^1$ is isopropyl, $R^2$ is methyl, $R^3$ is methyl, and the enantiomerically resolved mixture has an enantiomeric excess of the R enantiomer of the compound of Formula (I).

In certain embodiments, the enantiomerically resolved mixture has an enantiomeric excess of either the R-enantiomer of a compound of Formula (I) or the S-enantiomer of the compound of Formula (I), which exhibits an at least about 90% e.e., at least about 92% e.e., at least about 94% e.e., at least about 96% e.e., at least about 98% e.e., and in certain embodiments at least about 99% e.e.

Enantiomeric resolution of racemic compounds of Formula (I) can be accomplished using an enzyme such as an esterase, a protease, or a lipase. An example of a useful esterase is porcine liver esterase. Examples of useful lipases include *Candida rugosa, Candida cylindracea, Candida antarctica* lipase A, and *Candida antarctica* lipase B. Other potentially useful enzymes are known in the art and can be identified using routine screening methods. The enzymatic resolution can be carried out in an appropriate solvent or cosolvent at an appropriate temperature such as from about 5° C. to about 60° C., and in certain embodiments, from about 20° C. to about 27° C. The enzyme may be suspended in the solvent or immobilized on a support. Examples of useful solvents include isopropyl ether and methyl-tert-butyl ether (MTBE), and about 1% water may be useful as a cosolvent. The reaction can be continued for from about a few hours to about several days until a desired enantiomeric enrichment and/or yield is obtained. The reaction conditions may be selected and optimized using known methods.

Chemical structures of certain racemic acyloxyalkylthiocarbonates and the ability of certain enzymes to enantiomerically resolve the acyloxyalkylthiocarbonates are shown in FIG. 3 and FIG. 4, respectively.

Methods provided by the present disclosure include methods of synthesizing an enantiomerically enriched NHS-acyloxyalkylcarbonate of Formula (II), comprising:

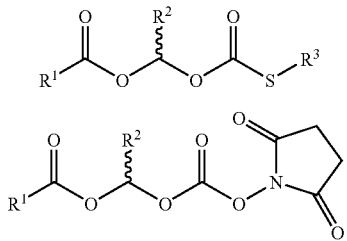

reacting an enantiomeric mixture of a compound of Formula (I) with an enzyme to provide an enantiomerically enriched mixture having at least 90% enantiomeric excess of one isomer of the compound of Formula (I), wherein $R^1$ is chosen from $C_{1-6}$ alkyl, $C_{3-6}$ cycloalkyl, phenyl, substituted phenyl, and $C_{7-9}$ phenylalkyl; $R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-4}$ alkyl, $C_{3-6}$ cycloalkyl, phenyl, substituted phenyl, and $C_{7-9}$ phenylalkyl; and reacting the enantiomerically enriched mixture having at least 90% enantiomeric excess of one isomer of the compound of Formula (I) with N-hydroxysuccinimide to provide the enantiomerically enriched mixture of the compound of Formula (II).

Coupling of an enantiomerically enriched acyloxyalkylthiocarbonate of Formula (I) with N-hydroxysuccinimide may be accomplished following the protocols described in Gallop et al., U.S. Pat. No. 7,227,028. For example, a compound of Formula (II) may be obtained by contacting a thiocarbonate compound of Formula (I) with an oxidant in the presence of N-hydroxysuccinimide.

In certain embodiments, the oxidant is a peroxy acid, a peroxide, ozone or oxygen. In certain embodiments, the oxidant is a stoichiometric or catalytic amount of a transition metal compound. In certain embodiments, the oxidant is a peroxy acid, a peroxide, ozone or oxygen with a catalytic amount of a transition metal compound. Examples of peroxy acids useful in the synthesis of NHS-acyloxyalkylcarbonates of Formula (II) include peroxyacetic acid, m-chloroperoxybenzoic acid, peroxytrifluoroacetic acid, peroxydifluoroacetic acid, peroxyfluoroacetic acid, peroxytrichloroacetic acid, peroxydichloroacetic acid, peroxychloroacetic acid, peroxytribromoacetic acid, peroxydibromoacetic acid, peroxybromoacetic acid, peroxychlorodifluoroacetic acid, peroxypentafluoropropionic acid, peroxybenzoic acid, p-fluoroperoxybenzoic acid, pentafluoroperoxybenzoic acid, p-trifluoroperoxybenzoic acid, o-nitroperoxybenzoic acid, m-nitroperoxybenzoic acid, p-nitroperoxybenzoic acid, 3,5-dinitroperoxybenzoic acid, monoperoxysuccinic acid, monoperoxymaleic acid, monoperoxy-o-phthalic acid, peroxytrifluoromethanesulfonic acid, peroxymethanesulfonic acid, p-tolueneperoxysulfonic acid, peroxybenzene sulfonic acid and salts thereof. In certain embodiments, the peroxy acid is chosen from peroxyacetic acid, m-chloroperoxybenzoic acid, monoperoxy-o-phthalic acid, monoperoxymaleic acid, peroxytrifluoroacetic acid or salts thereof. In other embodiments, the peroxy acid is peroxyacetic acid, m-chloroperoxybenzoic acid, magnesium monoperoxy-o-phthalate, and salts thereof. In certain embodiments, the peroxy acid may be synthesized by contacting a urea-hydrogen peroxide complex with an acid anhydride. In certain embodiments, the peroxy acid may be synthesized by contacting a urea-hydrogen peroxide complex with maleic anhydride.

In certain embodiments, the molar ratio of oxidant to an acyloxyalkyl thiocarbonate of Formula (I) is from about 10:1 to about 1:1. In certain embodiments, the molar ratio of oxidant to a thiocarbonate of Formula (I) is from about 3:1 to about 1:1.

In certain embodiments, a solvent is used in the synthesis of NHS-acyloxyalkylcarbonates of Formula (II). Useful solvents for the reaction include acetic acid, dichloromethane, dichloroethane, chloroform, ethyl acetate, toluene, chlorobenzene, xylene, acetonitrile, methyl tert-butyl ether, cyclohexane, and a mixture of any of the foregoing. In certain embodiments, the solvent is chosen from acetic acid, dichloromethane, dichloroethane, and a mixture of any of the foregoing.

In certain embodiments, the synthesis of NHS-acyloxyalkylcarbonates of Formula (II) may be carried out a temperature from about −20° C. to about 80° C., from about −20° C. to about 25° C., and in certain embodiments, from about 25° C. to about 60° C.

In certain embodiments, synthesis of NHS-acyloxyalkylcarbonates of Formula (II) may be performed in the presence of an inorganic base such as an alkali metal bicarbonate or alkali metal carbonate salt, and in certain embodiments, sodium bicarbonate. In certain embodiments, the synthesis of NHS-acyloxyalkylcarbonates of Formula (II) may be performed in the presence of an organic base such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, or 1,5-diazabicyclo[4.3.0]undec-7-ene. In other embodiments, the organic base is chosen from triethylamine, diisopropylethylamine, N-methylmorpholine, and pyridine. In certain embodiments, synthesis of NHS-acyloxyalkylcarbonates of Formula (II) may be performed in the absence of a base.

In certain embodiments, the enantiomerically resolved mixture has an enantiomeric excess of either the R-enantiomer of a compound of Formula (II) or the S-enantiomer of the compound of Formula (II), which exhibits an at least about 90% e.e., at least about 92% e.e., at least about 94% e.e., at least about 96% e.e., at least about 98% e.e., and in certain embodiments at least about 99% e.e.

Methods provided by the present disclosure include synthesizing a compound of Formula (III), comprising:

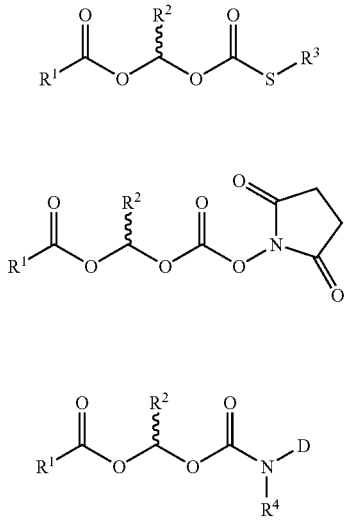

reacting an enantiomeric mixture of a compound of Formula (I) with an enzyme to provide an enantiomerically enriched mixture having at least 90% enantiomeric excess of one isomer of the compound of Formula (I), wherein $R^1$ is chosen from $C_{1-6}$ alkyl, $C_{3-6}$ cycloalkyl, phenyl, substituted phenyl, and $C_{7-9}$ phenylalkyl; $R^2$ is chosen from $C_{1-4}$ alkyl, $C_{3-6}$ cycloalkyl, phenyl, substituted phenyl, and $C_{7-9}$ phenylalkyl; $R^3$ is chosen from $C_{1-4}$ alkyl, $C_{3-6}$ cycloalkyl, phenyl, substituted phenyl, and $C_{7-9}$ phenylalkyl; and reacting the enantiomerically enriched mixture having at least 90% enantiomeric excess of one isomer of the compound of Formula (I) with N-hydroxysuccinimide to provide the enantiomerically enriched mixture of the corresponding compound of Formula (II); and reacting the enantiomerically enriched mixture of the compound of Formula (II) with a drug, D-NHR$^4$, comprising at least one primary or secondary amine group to provide the compound of Formula (III), wherein -D is the drug without the at least one primary or secondary amine group and $R^4$ is chosen from hydrogen or a group of the secondary amine.

In certain embodiments, the enantiomerically resolved mixture has an enantiomeric excess of either the R-enantiomer of a compound of Formula (III) or the S-enantiomer of the compound of (III), which exhibits an at least about 90% e.e., at least about 92% e.e., at least about 94% e.e., at least about 96% e.e., at least about 98% e.e., and in certain embodiments at least about 99% e.e.

In certain embodiments of methods of synthesizing compounds of Formula (III), the drug is chosen from R-baclofen and pregabalin. In certain embodiments, methods provided by the present disclosure may be used for the preparation of (3R)-4-{[(1S)-2-methyl-1-(2-methylpropanoyloxy)propoxy]carbonylamino}-3-(4-chlorophenyl)butanoic acid; 1-(R)-3-({[1-(2-methylpropanoyloxy)ethoxy]carbonylamino}methyl) (3S)-5-methylhexanoic acid; or a pharmaceutically acceptable salt of any of the foregoing.

In certain embodiments, methods provided by the present disclosure may be used for the preparation of a 1-(acyloxy)-alkyl carbamate prodrug of R-baclofen of Formula (a):

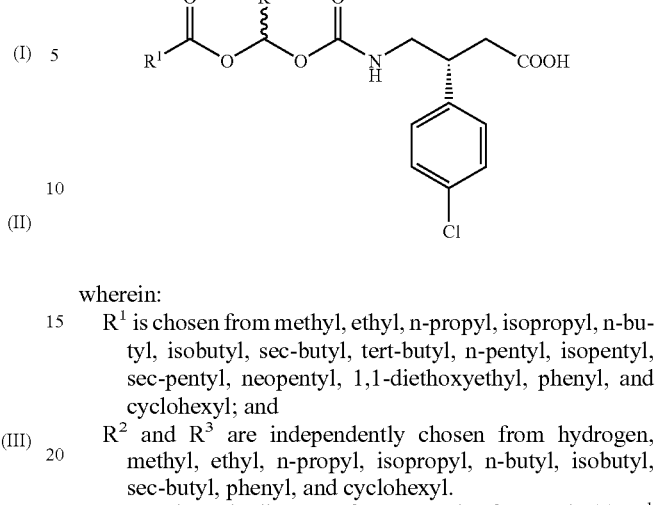

wherein:
 $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and
 $R^2$ and $R^3$ are independently chosen from hydrogen, methyl, ethyl, n-propyl, isopropyl, n-butyl, isobutyl, sec-butyl, phenyl, and cyclohexyl.

In certain embodiments of compounds of Formula (a), $R^1$ is isopropyl, and $R^2$ is isopropyl.

In certain embodiments of compounds of Formula (a), the carbon to which $R^2$ is bonded is of the S-configuration.

In certain embodiments of compounds of Formula (a), the carbon to which $R^2$ is bonded is of the R-configuration.

In certain embodiments of compounds of Formula (a), the compound is (3R)-4-{[(1S)-2-methyl-1-(2-methylpropanoyloxy)propoxy]carbonylamino}-3-(4-chlorophenyl)butanoic acid or a pharmaceutically acceptable salt thereof, or a pharmaceutically acceptable solvate of any of the foregoing.

In certain embodiments of methods of synthesizing compounds of compounds of Formula (III), the drug is R-baclofen, $R^1$ is isopropyl, $R^2$ is isopropyl, the enzyme is *Candida antarctica* lipase A, and the compound of Formula (III) is (3R)-4-{[(1S)-2-methyl-1-(2-methylpropanoyloxy)propoxy]carbonylamino}-3-(4-chlorophenyl)butanoic acid:

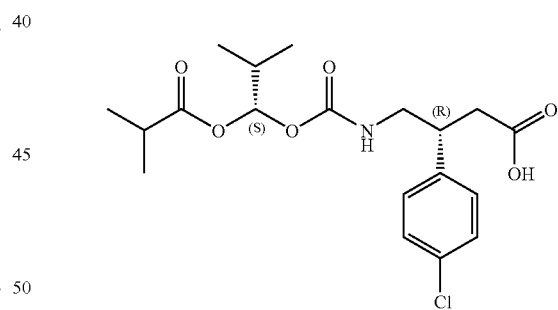

In certain embodiments, methods provided by the present disclosure may be used for the preparation of a 1-(acyloxy)-alkyl carbamate prodrug of pregabalin of Formula (b):

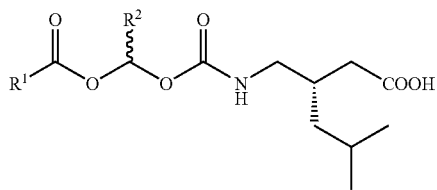

wherein:

R¹ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl; and R² is chosen from hydrogen, methyl, ethyl, n-propyl, isopropyl, n-butyl, isobutyl, sec-butyl, phenyl. and cyclohexyl.

In certain embodiments of compounds of Formula (b), R¹ is isopropyl, and R² is methyl.

In certain embodiments of compounds of Formula (b), the carbon to which R² is bonded is of the S-configuration.

In certain embodiments of compounds of Formula (b), the carbon to which R² is bonded is of the R-configuration.

In certain embodiments of compounds of Formula (b), the compound is 1-(R)-3-({[1-(2-methylpropanoyloxy)ethoxy]carbonylamino}methyl) (3S)-5-methylhexanoic acid or a pharmaceutically acceptable salt thereof, or a pharmaceutically acceptable solvate of any of the foregoing.

In certain embodiments of methods of synthesizing a compound of compounds of Formula (III), the drug is pregabalin, R¹ is isopropyl, R² is methyl, the enzyme is *Candida antarctica* lipase B, and the compound of Formula (III) is 3-({[(1R)-1-(2-methylpropanoyloxy)ethoxy]carbonylamino}methyl) (3S)-5-methylhexanoic acid:

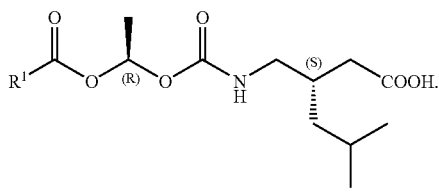

Conversion of a compound of Formula (I) to the corresponding NHS-acyloxyalkylcarbonate of Formula (II) and coupling with a drug can be accomplished, for example, following the protocols described in Gallop et al., U.S. Pat. No. 7,227,028, which provide the free acid form of the corresponding prodrug of Formula (III). For example, a NHS-acyloxyalkyl carbonate of Formula (II) or a salt thereof may be reacted with a primary or secondary amine-containing drug of formula D-NHR⁴ or a salt thereof to provide a compound of Formula (III) as shown in Scheme 1.

Scheme 1

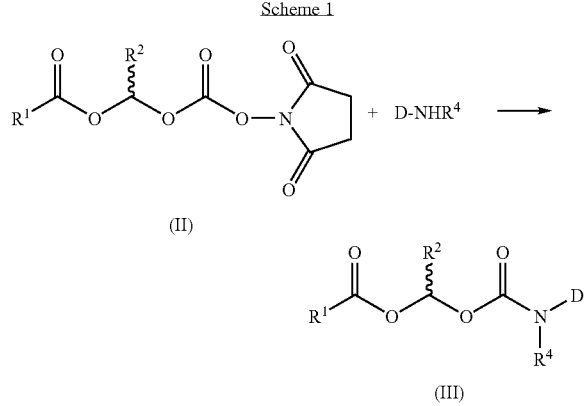

wherein R¹ and R² are as defined herein, and R⁴ is chosen from hydrogen and a moiety of a secondary amine-containing drug D-NHR⁴. Methods of synthesizing 1-(acyloxy)-alkyl carbamate prodrugs from 1-(acyloxy)alkyl N-hydroxysuccinimidyl carbonate intermediates are disclosed in Gallop et al., U.S. Pat. Nos. 6,818,787, 6,927,036, 6,972,341, 7,186,855, and 7,227,028; Raillard et al., U.S. Pat. No. 7,232,924; and Gallop and Bhat, WO 2005/010011, each of which is incorporated by reference in its entirety.

In certain embodiments, the reaction depicted in Scheme 1 may be carried out in an appropriate solvent such as, for example, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, or combinations of any of the foregoing. In certain embodiments, the solvent is chosen from acetone, acetonitrile, dichloromethane, toluene, tetrahydrofuran, pyridine, methyl tert-butyl ether, methanol, ethanol, isopropanol, water, and combinations of any of the foregoing. In certain embodiments, the solvent is a mixture of acetonitrile and water. In certain embodiments, the solvent is a mixture of acetonitrile and water, with a volume ratio of acetonitrile to water from about 1:5 to about 5:1. In certain embodiments, the solvent is a mixture of methyl tert-butyl ether and water. In certain embodiments, the solvent is a mixture of methyl tert-butyl ether and water, with a volume ratio of methyl tert-butyl ether to water from about 20:1 to about 2:1. In certain embodiments, the solvent is a mixture of methyl tert-butyl ether and water, wherein the methyl tert-butyl ether contains from about 10% to about 50% acetone by volume. In certain embodiments, the solvent is chosen from dichloromethane, water, and a combination thereof. In certain embodiments, the solvent is a biphasic mixture of dichloromethane and water. In certain embodiments, the solvent is a biphasic mixture of dichloromethane and water containing from about 0.001 equivalents to about 0.1 equivalents of a phase transfer catalyst. In certain embodiments, the phase transfer catalyst is a tetraalkylammonium salt. In certain embodiments, the phase transfer catalyst is a tetrabutylammonium salt.

In certain embodiments, the reaction depicted in Scheme 1 may be carried out at a temperature from about −20° C. to about 40° C., from about −20° C. to about 25° C., from about 0° C. to about 25° C., and in certain embodiments, from about 25° C. to about 40° C.

In certain embodiments, the reaction depicted in Scheme 1 may be performed in the absence of a base. In certain embodiments, the reaction depicted in Scheme 1 may be performed in the presence of an inorganic base such as an alkali metal bicarbonate or an alkali metal carbonate salt, and in certain embodiments, the inorganic base is sodium bicarbonate. In certain embodiments, the reaction depicted in Scheme 1 may performed in the presence of an organic base such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene, and in certain embodiments, the organic base is chosen from triethylamine, diisopropylethylamine, N-methylmorpholine, and pyridine.

Figure 2:
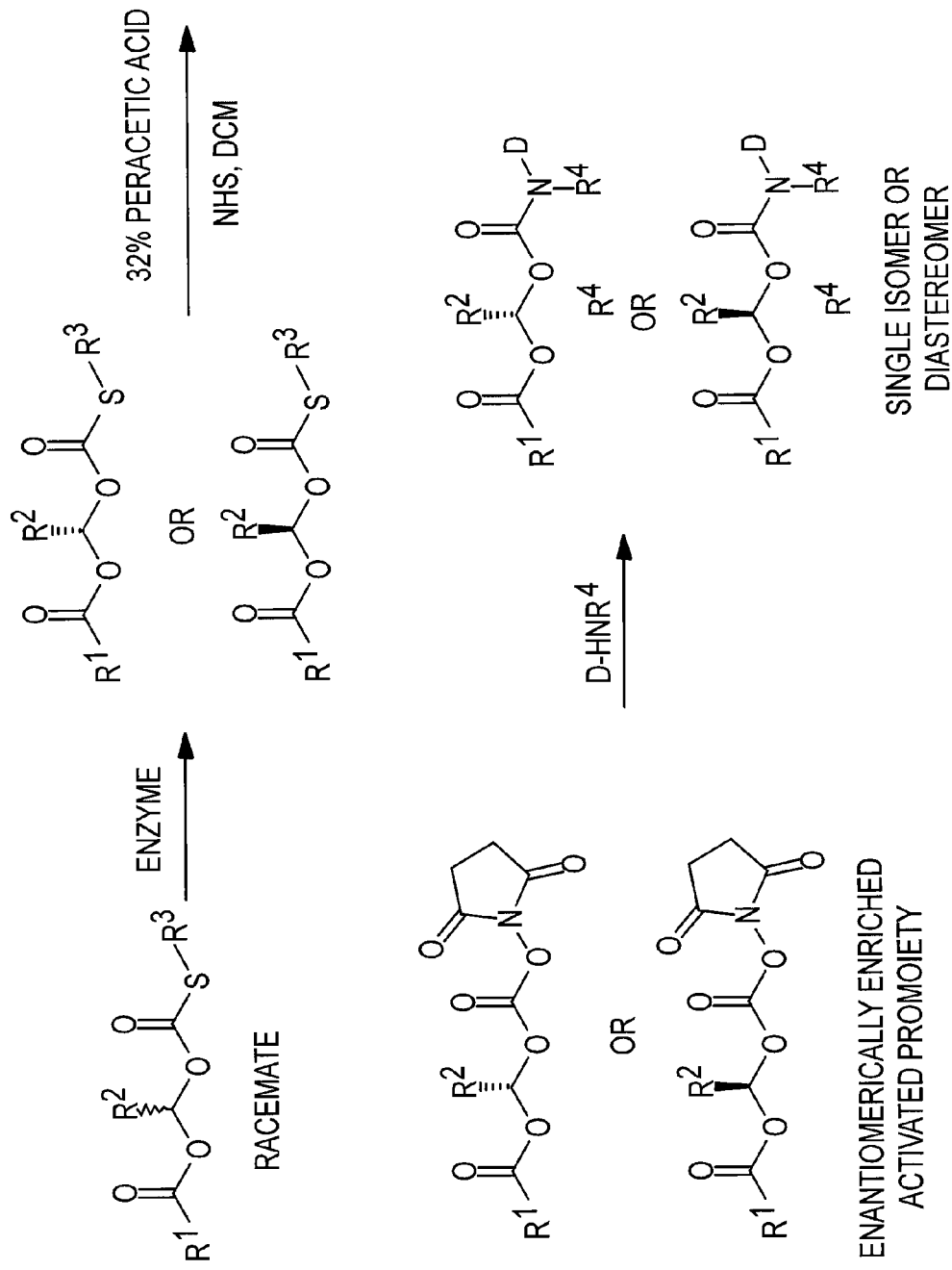
FIG. 2 shows a reaction sequence using enzymatic resolution of acyloxyalkyl thiocarbonate prodrug precursors to provide enantiomerically or diastereomerically enriched acyloxyalkyl carbamate prodrugs.
Figure 5:
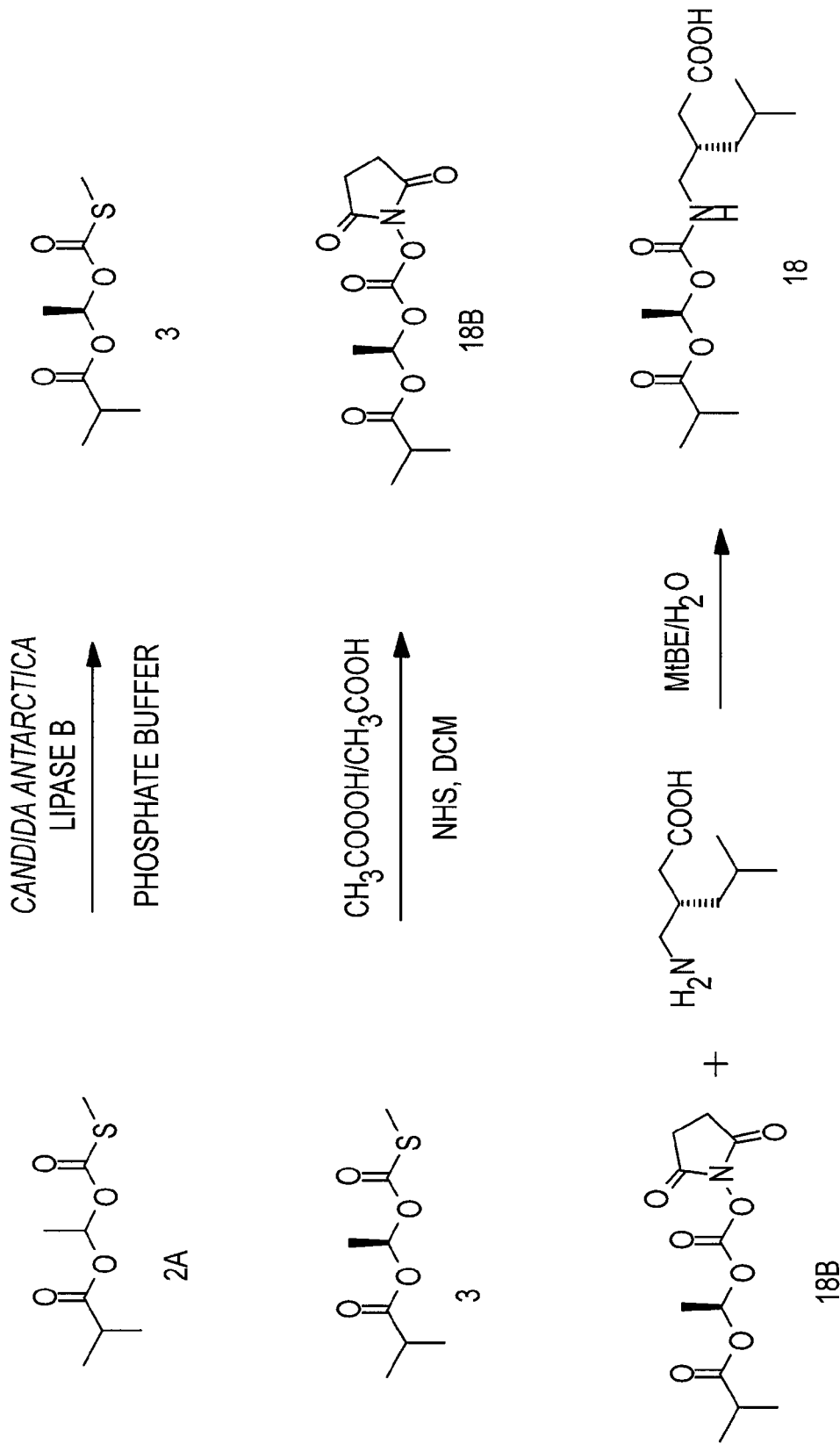
FIG. 5 shows an example of the synthesis of the pregabalin prodrug 3-({[(1R)-1-(2-methylpropanoyloxy)ethoxy]carbonylamino}methyl)(3S)-5-methylhexanoic acid.

The general synthetic methods provided by the present disclosure are shown in FIG. 2. A general synthetic scheme for 3-({[(1R)-1-(2-methylpropanoyloxy)ethoxy]carbonylamino}methyl)(3S)-5-methylhexanoic acid is shown in FIG. 5.

Intermediates

Compounds of the present disclosure include acyloxyalkylthiocarbonates of Formula (I) prepared by steps comprising reacting an enantiomeric mixture of the compound of Formula (I) with an enzyme to provide an enantiomerically enriched mixture of a compound of Formula (I) having at least 90% enantiomeric excess of one enantiomer of the compound of Formula (I), wherein $R^1$ is chosen from $C_{1-6}$ alkyl, $C_{3-6}$ cycloalkyl, phenyl, substituted phenyl, and $C_{7-9}$ phenylalkyl; $R^2$ is chosen from $C_{1-4}$ alkyl $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl.

1-(Acyloxy)-Alkyl Carbamate Prodrugs

Compounds provided by the present disclosure include compounds of Formula (III) or a pharmaceutically acceptable salt thereof, or a pharmaceutically acceptable solvate of any of the foregoing, prepared by the methods disclosed herein. Compounds of Formula (III) prepared according to the disclosed methods may be included in pharmaceutical compositions, which further comprise at least one pharmaceutically acceptable vehicle.

Compounds of Formula (III) or a pharmaceutically acceptable salt thereof or a pharmaceutically acceptable solvate of any of the foregoing obtained by the methods disclosed herein or a pharmaceutical composition thereof may be used in therapeutic application for treatment of an appropriate disease.

Compounds of Formula (III) in which D-NHR$^4$ is pregabalin and pharmaceutical compositions thereof may be used in the treatment of movement disorders, gastrointestinal disorders, psychotic disorders, mood disorders, anxiety disorders, sleep disorders, pulmonary disorders, neurodegenerative disorders, inflammatory disease, neuropathic pain, musculoskeletal pain, migraine, hot flashes, faintness attacks, urinary incontinence, ethanol withdrawal syndrome, and premature ejaculation. Pregabalin has also shown efficacy in controlled studies for treating neuropathic pain of varying etiologies, as well as depression, anxiety, psychosis, faintness attacks, hypokinesia, cranial disorders, neurodegenerative disorders, panic disorders, inflammatory disease, insomnia, gastrointestinal disorders, urinary incontinence and ethanol withdrawal syndrome (Magnus, *Epilepsia* 1999, 40, S66-72). The pharmacological activity of (3S)-aminomethyl-5-hexanoic acid is believed to be effected through binding to the $\alpha 2\delta$ subunit of voltage-gated calcium channels and the concomitant reduction in the synaptic release of neurotransmitters such as noradrenaline, glutamate, and substance P (Taylor et al., *Epilepsy Res* 2007, 73, 137-50). Accordingly, administering 1-(acyloxy)-alkyl carbamate prodrugs of pregabalin can be expected to be useful in treating diseases and disorders associated with $\alpha 2\delta$ subunit of voltage-gated calcium channels. In clinical trials, (3S)-aminomethyl-5-hexanoic acid has been shown to be effective in treating diseases and disorders including, for example, perioperative and post-operative pain (Dahl et al., *Acta Anaesthesiol Scand* 2004, 48, 1130-1136); musculoskeletal and neuropathic pain (Gallop et al., WO 02/100347; Zareba, *Drugs Today* 2005, 41(8), 509-16; and Blommel and Blommel, *Am J Health Syst Pharm* 2007, 64(14), 1475-82); chemotherapy-induced pain (Rao et al., *Cancer* 2007, 110(9), 2110-8; and Saif and Hashmi, *Cancer Chemother Pharmacol* 2008, 61, 349-354); general anxiety disorder (Rickels et al., *Arch Gen Psychiatry* 2005, 62, 1022-1030); anxiety (Pohl et al., *J Clin Psychopharmacol* 2005, 25, 151-8); post-herpetic neuralgia and painful diabetic peripheral neuropathy (Freynhagen et al., *Pain* 2005, 115, 254-63); sleep disorders (Sabatowski et al., *Pain* 2004, 109, 26-35; and Hindmarch et al., *Sleep* 2005, 28(2), 187-93); ethanol withdrawal syndrome (Becker et al., *Alcohol & Alcoholism* 2006, 41(4), 399-406); fibromyalgia (Crofford et al., *Arthritis and Rheumatism* 2005, 52, 1264-73); restless legs syndrome (Sommer et al., *Acta Neruol Scand* 2007, 115(5), 347-50); pain associated with spinal cord injury (Siddall et al., *Neurology* 2006, 67(10), 1792-800); social phobia (Pande et al., *J Clin Psychopharmacol* 2004, 24(2), 141-149); urinary incontinence (Barrett US 2005/0090550; and Segal et al., WO 00/61135); hot flashes (Guttuso, *Neurology* 2000, 54, 2161-2163; Loprinzi et al., *Mayo Clin. Proc.* 2002, 77, 1159-1163; Jeffery et al., *Ann. Pharmacother.* 2002, 36, 433-435; and Guttuso et al., *Obstet. Gynecol.* 2003, 101, 337-345); rapid ejaculation (Taylor et al., US 2004/0176456), vulvodynia (Ben-David et al., *Anesth, Analg.* 1999, 89, 1459-60); and others.

Cundy, U.S. patent application Ser. No. 12/139,057 filed Jun. 13, 2008 (which is incorporated by referenced in its entirety) discloses the use of 1-(acyloxy)-alkyl carbamate prodrugs of GABA analogs such as pregabalin for treating spasticity; Trân, WO 2007/027477 and WO 2007/027476 (each of which is incorporated by reference in its entirety) discloses the use of 1-(acyloxy)-alkyl carbamate prodrugs of GABA analogs for treating vulvodynia and premature ejaculation, respectively; Barrett and Cundy, US 2008/0161393 (which is incorporated by reference in its entirety) disclose the use of 1-(acyloxy)-alkyl carbamate prodrugs of GABA analogs for treating migraine, fibromyalgia, amyotrophic lateral sclerosis, irritable bowel syndrome, social phobia, Parkinson's disease, asthma, cough, or chronic obstructive pulmonary disease; and the use of 1-(acyloxy)-alkyl carbamate prodrugs of GABA analogs for treating restless legs syndrome, hot flashes, and urinary incontinence is disclosed in Barrett and Canafax, US 2005/0192353, Barrett and Gallop, US 2004/0254246, and Barrett, US 2005/0090550 (each of which is incorporated by reference in its entirety), respectively.

Compounds of Formula (III) in which D-NHR$^4$ is R-baclofen and pharmaceutical compositions thereof may be used in the treatment of spasticity, gastro-esophageal reflux disease, emesis, cough, narcotic addiction or abuse, alcohol addiction or abuse, nicotine addiction or abuse, urinary incontinence, neuropathic pain, and musculoskeletal pain such as painful lower back spasm.

A principal pharmacological effect of baclofen in mammals is reduction of muscle tone and the drug is frequently used in the treatment of spasticity (Price et al., *Nature* 1984, 307, 71-4). Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient. Baclofen is also useful in controlling gastro-esophageal reflux disease (van Herwaarden et al., *Aliment. Pharmacol. Ther.* 2002, 16, 1655-62; Ciccaglione et al., *Gut* 2003, 52, 464-70; Andrews et al., U.S. Pat. No. 6,117,908; and Fara et al., WO 02/096404); in promoting alcohol abstinence in alcoholics (Gessa et al., WO 01/26638); in promoting smoking cessation (Gessa et al., WO 01/08675); in reducing addiction liability of narcotic agents (Robson et al., U.S. Pat. No. 4,126, 684); in the treatment of emesis (Bountra et al., U.S. Pat. No. 5,719,185); as an anti-tussive for the treatment of cough (Kreutner et al., U.S. Pat. No. 5,006,560); in treating neuropathic pain such as trigeminal neuralgia (Bowsher, *Br. Med.*

Bull. 1991, 47(3), 655-66; Fromm et al., *Neurology* 1981, 31, 683-7; and Ringel and Roy, *Ann Neurol* 1987, 21(5), 514-5); and in treating musculoskeletal pain such as painful lower back spasm (Dapas et al., *Spine* 1985, 10(4), 345-9; and Raphael et al., *BMC Musculoskeletal Disorders* 2002, 3(17), Epub 2002 Jun. 20); tension-type headaches (Freitag, *CNS Drugs* 2003, 17(6), 373-81); and radiculopathy (Zuniga et al., *Anesthesiology* 2000, 92(3), 876-880). Cundy, U.S. patent application Ser. No. 12/139,057 filed Jun. 13, 2008 (incorporated by referenced herein in its entirety) disclose the use of 1-(acyloxy)-alkyl carbamate prodrugs of R-baclofen in combination with GABA analog prodrugs for treating spasticity, and Benson et al., U.S. application Ser. No. 10/266,169 filed Nov. 6, 2008 (which is incorporated by referenced in its entirety) disclose the use of 1-(acyloxy)-alkyl carbamate prodrugs of R-baclofen for treating neuropathic and musculoskeletal pain, including muscle spasms due to musculoskeletal conditions such as back spasm in the lumbar, thoracic and/or cervical regions.

In certain embodiments of compounds of Formula (III), a primary or secondary amine-containing drug, D-NHR$^4$, is chosen from acebutolol, adaprolol, adrenalone, adrogolide, aladapcin, alatrofloxacin, albendazole, albuterol, albutoin, alendronate, alestramustine, aletamine, alinidine, aliskiren, alizapride, alniditan, alprafenone, alprenolol, alprenoxime, altromycin A, altromycin C, amantadine, amidephrine, amifostine, amikacin, amiloride, aminolevulinic acid, a minorex, amlodipine, amosulalol, amoxapine, amphetamine, amphotericin B, amrubicin, amselamine, amthamine, anabasine, angiopeptin, anisperimus, aprinocid, arbekacin, arbutamine, argiopine, arotinolol, aspartame, aspoxicillin, atenolol, avizafone, azoxybacilin, baclofen, bactobolin, balanol, balofloxacin, bambuterol, bamethan, baogongteng A, barusiban, batoprazine, becampanel, befunolol, belactosin A, belactosin C, benanomicin B, benazepril, berlafenone, betahistine, betaxolol, bevantolol, biemnidin, binospirone, bisoprolol, boholmycin, bopindolol, brasilicardin A, brinzolamide, bunolol, bupropion, butabindide, buteranol, butofilolol, butopamine, butoxamine, caldaret, cambendazole, cambrescidins, caprazamycin, capromorelin, capsavanil, carbidopa, carbuterol, carteolol, carvedilol, cefaclor, cefcanel, cefcanel daloxate, cefminox, cefprozil, ceftizoxime, celiprolol, ceranapril, cetefloxacin, chlorotetain, chlorternine, cilazapril, cimaterol, cimetidine, cinacalcet, ciprofloxacin, circinamide, cisapride, cispentacin, clonidine, cloranolol, clorprenaline, colterol, cyclobendazole, cyclothialidine, cystamine, cystocin, cytaramycin, dabelotine, dactimicin, dalargin, dalbavancin, daunorubicin, D-cycloserine, decaplanin, deferoxamine, delapril, delavirdine, delfaprazine, delucemine, demexiptiline, denopamine, deoxymethylspergualin, deoxynegamycin, deoxynojirimycin, deoxyspergualin, desipramine, desloratadine, deterenol, dexpropranolol, diacetolol, dihydrexidine, dilevalol, dimethoxyphenethylamine, dinapsoline, dirithromycin, dobutamine, donitriptan, dopamine, dopexamine, doripenem, dorzolamide, doxorubicin, droxidopa, droxinavir, duloxetine, duramycin, ecenofloxacin, ecteinascidins, efegatran, eflornithine, eglumegad, elarofiban, enalapril, enalkiren, enkastins, enoxacin, enviroxime, ephrinephrine, epibatidine, epirubicin, epithalon, eremomycin, ersentilide, ertapenem, esafloxacin, esmolol, esperamicin A1, etintidine, etryptamine, examorelin, exaprolol, exatecan, ezlopitant, fasudil, fenbendazole, fenfluramine, fenmetazole, fenoldopam, fenoterol, fenyripol, fepradinol, ferulinolol, flecamide, flubendazole, fludorex, fluoxetine, fluparoxan, fluvirucin B2, fluvoxamine, formoterol, fortimicin A, fosopamine, frovatriptan, fudosteine, gaboxadol, galarubicin, gatnon, garenoxacin, garomefrine, gatifloxacin, gemifloxacin, gilatide, giracodazole, gludopa, halofuginone, helvecardin A, helvecardin B, hispidospermidin, histaprodifen, hydrostatin A, ibopamine, ibutamoren, icadronate, icatibant, icofungipen, idarubicin, imidapril, immepip, immepyr, immucillin-H, impentamine, indeloxazine, inogatran, isodoxorubicin, isofagomine, janthinomycins, kahalalide F, kaitocephalin, kanamycin, ketamine, L-4-oxalysine, labetalol, ladostigil, lagatide, landiolol, lanicemine, lanomycin, lapatinib, lazabemide, L-dopa, lenapenem, lerisetron, leurubicin, leustroducsin A, leustroducsin B, leustroducsin C, leustroducsin H, levobunolol, L-histidinol, L-homothiocitrulline, lisinopril, litoxetine, lobendazole, lobophorin A, loracarbef, lotrafiban, L-thiocitrulline, lubazodone, lysobactin, mabuterol, manzamines, maprotiline, maropitant, mebendazole, mecamylamine, mefloquine, melagatran, meluadrine, memantine, mepindolol, meropenem, mersacidin, metaproterenol, metaraminol, metazoline, methoctramine, methyldopa, methylphenidate, metoclopramide, metolol, metoprolol, metyrosine, mexiletine, michellamine B, micronomicin, midafotel, midaxifylline, mideplanin, milacamide, milnacipran, mitoxantrone, moexipril, mofegiline, moxifloxacin, mureidomycins, mycestericin E, n-[3(R)-[2-piperidin-4-yl)ethyl]-2-piperidone-1-yl]acetyl-3(R)-methyl-β-alanine, nadolol, napsamycins, nardeterol, N-desmethylmilameline, nebivolol, neboglamine, nebracetam, nepicastat, neramexane, neridronate, nemifidide, nifedipine, nimodipine, nipradilol, noberastine, noberastine, nocodazole, nolomirole, norepinephrine, norfloxacin, nomicotine, nortopixantrone, nortriptyline, nuvanil, oberadilol, octreotide, olamufloxacin, olcegepant, olradipine, orbifloxacin, orienticins, oritavancin, oseltamivir, osutidine, ovothiol A, ovothiol B, oxfendazole, oxibendazole, oxmetidine, oxolide, oxprenolol, pafenolol, palau'amine, palindore, pamatolol, pamidronate, papuamide A, papuamide B, parbendazole, parodilol, paromomycin, paroxetine, paroxetine, pasireotide, pazufloxacin, pelagiomicin C, penbutolol, perindopril, phendioxan, phospholine, picumeterol, pindolol, p-iodorubidazone, pipedimic acid, pirbuterol, pixantrone, pluraflavin A, pluraflavin B, poststatin, practolol, pradimicin, pradimicin B, pradimicin D, pradimicin E, pradimicin FA-2, pradofloxacin; pramipexole, pranidipine, prazosin, pregabalin, premafloxacin, prenalterol, primidolol, prisotinol, prizidilol, procainamide, procaterol, propafenone, propanolol, protriptyline, proxodolol, pseudoephedrine, pyloricidin B, pyridazomycin, quinapril, quinterenol, R-(+)-aminoindan, ralfinamide, ramipril, ramoplanins, ranitidine, rasagiline, ravidomycin, reboxetine, remacemide, repinotan, reproterol, restricticin, rhodopeptins, rilmazafone, rimiterol, risotilide, ritodrine, ruboxyl, sabarubicin, safinamide, safingol, salbostatin, salbutamol, salmeterol, sampatrilat, sarizotan, seglitide, seproxetine, seraspenide, sertraline, setazindol, sezolamide, sibanomicin, sibenadet, silodosin, sitafloxacin, sacoromycin, solabegron, solpecainol, soterenol, sparfloxacin, sperabillins, spinorphin, spisulosine, squalamine, styloguanidine, sulfinalol, sulfonterol, suloctidil, sulphazocine, sulphostin, sumanirole, tabilautide, tabimorelin, tafenoquine, tageflar, tolamolol, talibegron, tamsulosin, targinine, tazolol, tecalcet, telavancin, temocapril, terbutaline, tertatolol, tetrafibricin, tetrahydrazoline, tetrindol, theprubicin, thiabendazole, thiofedrine, thrazarine, tiamdipine, tiamenidine, tianeptine, tienoxolol, tigecycline, tilisolol, timolol, tinazoline, tiotidine, tipifamib, tiprenolol, tipropidil, tirofiban, tocamide, tolazoline, tomoxetine, topixantrone, tosufloxacin, tramazoline, trandolapril, tranexamic acid, tranylcypromine, triamterene, trovafloxacin, troxipide, tuftsin, tulathromycin B, tulobuterol, ubistatin, ulifloxacin, utibapril, vestipitant, vicenistatin, vigabatrin, vildagliptin, viloxazine, vofopitant, voglibose, xamoterol, ximelagatran, xylometazoline, zabiciprilat, zelandopam, ziconotide, zilpaterol, zorubicin, α-methyltryptophan, α-methylepinephrine, (−)-cicloprolol, (−)-nebivolol, (+)-isamoltan, (+)-sotalol, (R)-(+)-amlodipine, (S)-noremopamil, 1-ethyl-6-fluoro-1,21-aminoepothilone B, 4-dihydro-4-oxo-7-(1-piperazinyl)-1,4-dihydro-4-oxo-7-(piperazinyl)-3-quinolinecarboxylic acid, 7-oxostaurosporine, 8-napthyridine-3-carboxylic acid, and 1-cyclopropyl-6-fluoro-1. Other secondary or primary amine-containing drugs D-NHR[4] are described in various compendia available to a skilled chemist, such as, for example, the Merck Index, 14th Edition, 2006 or the Physicians Desk Reference, 62nd Edition, 2007. Accordingly, secondary or primary amine-containing drugs D-NHR[4] described in such references are encompassed by the present disclosure. The corresponding 1-(acyloxy)-alkyl carbamate prodrug synthesized according to the methods provided by the present disclosure and pharmaceutical compositions thereof may be used to treat a disease for which the parent secondary or primary amine-containing drug is therapeutically effective.

In certain embodiments, D-NHR[4] is chosen from alendronate, amifostine, rac-baclofen, R-baclofen, carbidopa, clonidine, ciprofloxacin, cisapride, daunorubicin, doxorubicin, fenoldopam, fenoterol, gabapentin, gentamycin, kanamycin, levodopa, meropenem, metazoline, neomycin, pamidronate, pregabalin, tobramycin, tranexamic acid, trovafloxacin, and vigabatrin. In certain embodiments, D-NHR[4] is chosen from R-baclofen and pregabalin. In certain embodiments, D-NHR[4] is a GABA analog as defined herein.

EXAMPLES

The following examples describe in detail enzymatic resolution of acyloxyalkyl thiocarbonates, enantiomerically or diasteromerically enriched compounds synthesized using the disclosed methods, and use of enzymatically resolved acyloxyalkyl thiocarbonates in the synthesis of acyloxyalkyl carbamate prodrugs. It will be apparent to those skilled in the art that many modifications, both to materials and methods, may be practiced without departing from the scope of the disclosure.

Description 1

General Experimental Protocols

All reagents and solvents were purchased from commercial suppliers and used without further purification or manipulation.

Proton NMR spectra (400 MHz) were recorded on a Varian AS 400 NMR spectrometer equipped with an autosampler and data processing computation. CDCl$_3$ (99.8% D), DMSO-d$^6$ (99.9% D), or MeOH-d$^4$ (99.8+% D) were used as solvents unless otherwise noted. The CHCl$_3$, DMSO-d$^5$, or MeOH-d$^3$ solvent signals were used for calibration of the individual spectra. Determination of enantiomeric excess (e.e.) of intermediates was accomplished by $^1$H NMR spectroscopy in the presence of the diamagnetic enantiomerically pure chiral co-solvent (R)-(−)-2,2,2-trifluoro-1-(9-anthryl)ethanol (Pirkle-alcohol) and in comparison with $^1$H NMR spectra of the corresponding racemic samples under similar conditions.

All thiocarbonates were synthesized by following a two-step reaction sequence. The enzymatic reactions were carried out using from about 5 wt-% to about 10 wt-% enzyme in water at room temperature with stirring or shaking. The progress of the reactions and enzyme selectivity was monitored using $^1$H-NMR with (R)-(−)-2,2,2-trifluoro-1-(9-anthryl)ethanol as the chiral solvating agent (e.g., Pirkle or Hoover reagents).

Enantiomeric excess was determined using chiral HPLC with a reverse phase column. For example, to determine enantiomeric excess, a Waters 2795 HPLC with a chiral Technologies ChiralCel OJ-RH 4.6×150 mm column was used. The column temperature was 35° C. and the mobile phases were (A) 20 mM potassium phosphate monobasic buffer (pH 2.5) and (B) 2% buffer/8% water/90% acetonitrile (ACN). Ten (10) μL of sample (1.0 mg/mL) was injected into the column and detected using a Waters 996 PDA at 210 nm.

The absolute configuration of the enzymatically resolved thiocarbonates was confirmed by derivatizing the thiocarbonates to compounds of known stereochemistry and comparing the retention times on a chiral HPLC column. For example, compounds having known stereochemistry were prepared using Baeyer-Villiger oxidation, according to the following scheme.

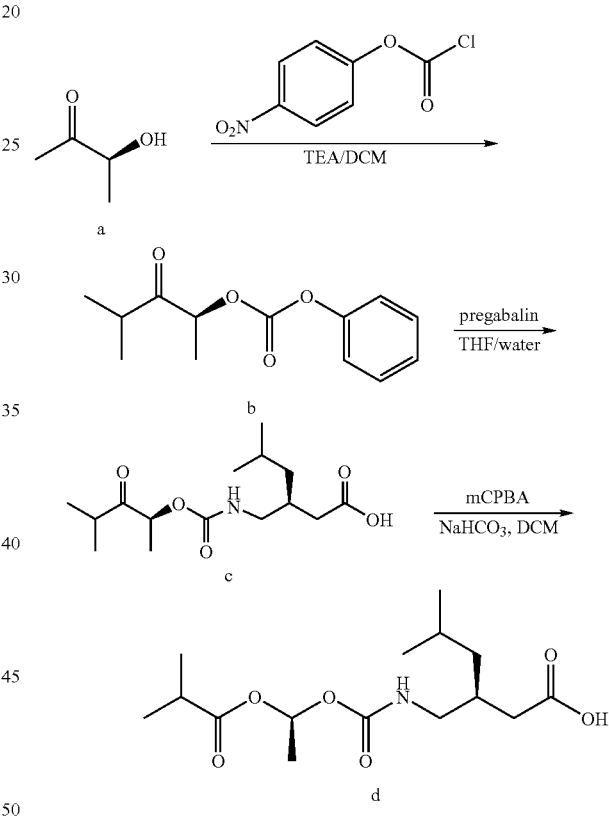

For example, 1-(S)-3-({[1-(2-methylpropanoyloxy)ethoxy]carbonylamino}methyl)(3S)-5-methylhexanoic acid (d) was prepared by reacting (2S)-2-hydroxy-4-methylpentan-3-one (a) and 4-nitrophenyl chloroformate in the presence of triethylamine (TEA) in dichloromethane (DCM) to provide (1S)-1,3-dimethyl-2-oxobutyl(4-nitrophenoxy)formate (b). (1S)-1,3-Dimethyl-2-oxobutyl(4-nitrophenoxy)formate was then reacted with pregabalin in a mixture of tetrahydrofuran (THF) and water to provide (3S)-3-{[((S)-1,3-dimethyl-2-oxobutoxy)carbonylamino]methyl}-5-methylhexanoic acid (c). Intermediate (c) was then reacted overnight with meta-chloroperoxybenzoic acid (mCPBA) (2.5 eq.) and sodium bicarbonate (NaHCO$_3$) (1 eq.) in dichloromethane (DCM) at room temperature to provide 1-(S)-3-({[1-(2-methylpropanoyloxy)ethoxy]carbonylamino}methyl)(3S)-5-methylhexanoic acid (d).

Other enantiomerically or diastereomerically pure compounds were prepared using similar methods and replacing (2S)-2-hydroxy-4-methylpentan-3-one with an appropriate compound having known and specific stereochemistry, and replacing pregabalin with an appropriate drug, such as gabapentin, baclofen, or others.

Example 1

Chloroalkylmethanethiocarbonates (1a-1c)

To a stirred solution of chloroalkyl-chloroformate in dichloromethane (DCM) was added a solution of sodium methanethiolate ($CH_3$—SNa) (1.0 eq.) in water at 0° C. and 0.02 eq. of tetrabutylammonium bromide. The reactants were stirred at 0° C. for 30 min and then diluted with dichloromethane (DCM). The dichloromethane layer was allowed to separate, then washed with water and brine, and dried with anhydrous sodium sulfate ($Na_2SO_4$). After rotary evaporation to remove the solvent, the corresponding chloroalkyl-methanethiocarbonate (1) was obtained.

1-Chloro-2-methylpropyl methylthioformate (1a): $^1$H-NMR (CDCl$_3$): δ 1.05 (d, J=5.6 Hz, 3H), 1.07 (d, J=5.6 Hz, 3H), 2.18 (m, 1H), 2.38 (s, 3H), 6.34 (d, J=5.6 Hz, 1H) ppm.

Chlorobutyl methylthioformate (1b): $^1$H-NMR (CDCl$_3$): δ 0.97 (t, J=7.6 Hz, 3H), 1.51 (sextet, J=7.6 Hz, 2H), 2.02 (m, 2H), 2.40 (s, 3H), 6.48 (t, J=6.0 Hz, 1H) ppm.

Chloroethyl methylthioformate (1c): $^1$H-NMR (CDCl$_3$): δ 1.80 (d, J=5.6 Hz, 3H), 2.37 (s, 3H), 6.57 (q, J=5.6 Hz, 1H) ppm.

Example 2

Racemic Acyloxyalkylmethanethiocarbonates (2a-2h)

A chloroalkylmethanethiocarbonate prepared according to Example 1 was added to a mixture of a carboxylic acid (4 eq.) and diisopropylethylamine (DIEA) (2 eq.). The mixture was stirred at 75° C. for 24 hrs. The mixture was then partitioned between water and methyl-tert-butyl ether (MTBE). The MTBE layer was washed three times with water, aqueous sodium bicarbonate (NaHCO$_3$), water, and brine, and then dried over anhydrous sodium sulfate (Na$_2$SO$_4$). After the solvent was removed by rotary evaporation the corresponding racemic acyloxyalkylmethane thiocarbonate (2) was obtained with 60-80% yield.

1-Methylthiocarbonyloxyethyl 2-methylpropanoate (2a): $^1$H-NMR (CDCl$_3$): δ 1.18 (d, J=7.0 Hz, 3H), 1.16 (d, J=7.6 Hz, 3H), 1.50 (d, J=5.6 Hz, 3H), 2.34 (s, 3H), 2.55 (septet, J=7.2 Hz, 1H), 6.92 (q, J=5.6 Hz, 1H) ppm. $^1$H-NMR with chiral solvating agent (R)-(−)-2,2,2-trifluoro-1-(9-anthryl)ethanol: δ 1.18 (m, 6H), 1.495 (d, J=5.2 Hz, 1.5H), 1.50 (d, J=5.6 Hz, 1.5H), 2.33 (s, 1.5H), 2.34 (s, 1.5H), 2.56 (septet, J=7.2 Hz, 0.5H), 2.56 (septet, J=7.2 Hz, 0.5H), 6.92 (q, J=5.6 Hz, 0.5H), 6.92 (q, J=5.6 Hz, 0.5H) ppm.

2-Methyl-1-methylthiocarbonyloxypropyl 2-methylpropanoate (2b): $^1$H-NMR (CDCl$_3$): δ 0.96 (d, J=6.8 Hz, 6H), 1.16 (d, J=6.8 Hz, 3H), 1.17 (d, J=6.8 Hz, 3H), 1.98-2.07 (m, 1H), 2.32 (s, 3H), 2.56 (septet, J=7.2 Hz, 1H), 6.67 (d, J=5.6 Hz, 1H) ppm. $^1$H-NMR with chiral solvating agent (R)-(−)-2,2,2-trifluoro-1-(9-anthryl)ethanol: δ 0.98 (d, J=6.8 Hz, 3H), 0.99 (d, J=6.8 Hz, 3H), 1.19 (d, J=7.2 Hz, 1.5H), 1.19 (d, J=6.8 Hz, 1.5H), 1.20 (d, J=6.8 Hz, 1.5H), 1.20 (d, J=7.2 Hz, 1.5H), 2.01-2.09 (m, 1H), 2.34 (s, 1.5H), 2.44 (s, 1.5H), 2.59 (septet, J=7.2 Hz, 0.5H), 2.594 (septet, J=6.8 Hz, 0.5H), 6.70 (d, J=5.6 Hz, 0.5H), 6.70 (d, J=5.2 Hz, 0.5H) ppm.

Methylthiocarbonyloxybutyl 2-methylpropanoate (2c): $^1$H-NMR (CDCl$_3$): δ 0.96 (t, J=7.2 Hz, 3H), 1.17 (m, 6H), 1.41 (sextet, J=7.2 Hz, 2H), 1.76 (m, 2H), 2.34 (s, 3H), 2.56 (m, 1H), 6.85 (t, J=6.0 Hz, 1H) ppm. $^1$H-NMR with chiral solvating agent (R)-(−)-2,2,2-trifluoro-1-(9-anthryl)ethanol: δ 0.96 (t, J=7.2 Hz, 3H), 1.18 (m, 6H), 1.42 (m, 2H), 1.78 (m, 2H), 2.34 (s, 1.5H), 2.34 (s, 1.5H), 2.57 (septet, J=7.2 Hz, 0.5H), 2.57 (septet, J=7.2 Hz, 0.5H), 6.86 (t, J=5.6 Hz, 0.5H), 6.86 (t, J=5.6 Hz, 0.5H) ppm.

2-Methyl-1-methylthiocarbonyloxypropyl butanoate (2d): $^1$H-NMR (CDCl$_3$): δ 0.96 (t, J=7.2 Hz, 3H), 0.97 (d, J=7.2 Hz, 3H), 0.98 (d, J=6.8 Hz, 3H), 1.68 (sextet, J=7.2 Hz, 2H), 2.04 (m, 1H), 2.3 (t, J=7.2 Hz, 2H), 2.34 (s, 3H), 6.70 (d, J=5.2 Hz, 1H) ppm. $^1$H-NMR with chiral solvating agent (R)-(−)-2,2,2-trifluoro-1-(9-anthryl)ethanol: δ 0.95 (t, J=7.2 Hz, 1.5H), 0.96 (t, J=7.2 Hz, 1.5H), 0.98 (d, J=6.8 Hz, 3H), 0.98 (d, J=7.2 Hz, 3H), 1.66 (sextet, J=7.2 Hz, 1H), 1.66 (sextet, J=7.2 Hz, 1H), 2.03 (m, 1H), 2.32 (m, 2H), 2.34 (s, 1.5H), 2.34 (s, 1.5H), 6.70 (d, J=5.2 Hz, 0.5H), 6.70 (d, J=5.2 Hz, 0.5H) ppm.

1-Methylthiocarbonyloxybutyl butanoate (2e): $^1$H-NMR (CDCl$_3$): δ 0.95 (m, 6H), 1.41 (sextet, J=7.2 Hz, 2H), 1.66 (m, 2H), 1.75 (m, 2H), 2.29 (m, 2H), 2.34 (s, 3H), 6.87 (t, J=5.6 Hz, 1H) ppm. $^1$H-NMR with chiral solvating agent (R)-(−)-2,2,2-trifluoro-1-(9-anthryl)ethanol: δ 0.95 (t, J=7.2 Hz, 1.5H), 0.95 (t, J=7.2 Hz, 1.5H), 0.96 (t, J=7.4 Hz, 3H), 1.40 (m, 2H), 1.65 (sextet, J=7.2 Hz, 1H), 1.66 (sextet, J=7.2 Hz, 1H), 1.77 (m, 2H), 2.31 (m, 2H), 2.34 (s, 1.5H), 2.34 (s, 1.5H), 6.87 (t, J=5.6 Hz, 1H) ppm.

2-Methyl-1-methylthiocarbonyloxypropyl acetate (2f): $^1$H-NMR (CDCl$_3$): δ 0.96 (d, J=7.0 Hz, 3H), 0.98 (d, J=7.0 Hz, 3H), 2.10 (s, 3H), 2.34 (s, 3H), 6.68 (d=5.2 Hz, 1H) ppm. $^1$H-NMR with chiral solvating agent (R)-(−)-2,2,2-trifluoro-1-(9-anthryl)ethanol: δ 0.98 (m, 6H), 2.04 (m, 1H), 2.08 (s, 1.5H), 2.09 (s, 1.5H), 2.34 (s, 1.5H), 2.34 (s, 1.5H), 6.69 (d, J=5.6 Hz, 0.5H), 6.69 (d, J=5.6 Hz, 0.5H) ppm.

Methylthiocarbonyloxyethyl benzoate (2g): $^1$H-NMR (CDCl$_3$): δ 1.65 (d, J=5.6 Hz, 3H), 2.35 (s, 3H), 7.20 (q, J=5.6 Hz, 1H), 7.45 (m, 2H), 7.58 (m, 1H), 8.06 (m, 2H) ppm.

2-Methyl-1-methylthiocarbonyloxyethyl benzoate (2h) $^1$H-NMR (CDCl$_3$): 1.07 (3H, d, J=6.8 Hz), 1.08 (3H, d, J=6.8 HZ), 2.18-2.23 (1H, m), 2.35 (3H, s), 6.97 (1H, d, J=5.2 Hz), 7.44 (2H, m), 7.58 (1H, m), 8.05 (2H, m).

Description 2

General Procedure for Enzymatic Hydrolysis in Aqueous Phase

A suspension of enzyme (5-10% by weight) in 50 mM pH 7.2 phosphate buffer (45 mL) and a racemic acyloxyalkyl-methanethiocarbonate (Example 2) (10 mmol) in isopropyl ether (5 mL) was shaken on a orbital shaker at room temperature (25° C.). The reaction was monitored by $^1$H-NMR using chiral solvating agent. After the reaction was complete the reaction mixture was filtered through a pad of CELITE® 545, followed by extraction with methyl-tert-butyl ether (MTBE), washed with water and brine, and dried over anhydrous sodium sulfate (Na$_2$SO$_4$). Following rotary evaporation to remove the solvents, the corresponding enzymatically resolved acyloxyalkylmethyl thiocarbonate was obtained.

Example 3

(1R)-Methylthiocarbonyloxyethyl 2-methylpropanoate (3)

A mixture of methylthiocarbonyloxyethyl-2-methylpropanoate (2a) (180 g) and lipase acrylic resin incorporating *Candida antarctica* lipase B (NOVOZYME® 435, Sigma-Aldrich) (8.0 g) in pH 7.2 phosphate buffered saline (1.6 L) was stirred at room temperature. The reaction was monitored by $^1$H-NMR using the chiral solvating agent (R)-(−)-2,2,2-trifluoro-1-(9-anthryl)ethanol. The reaction was complete in 16 hrs. The reaction mixture was diluted with ether, and the ether layer separated and filtered through a pad of CELITE® 545 to remove the enzyme. The ether supernatant was washed with water (5 times) and brine, and dried over anhydrous sodium sulfate ($Na_2SO_4$). After rotary evaporation, 90 g of the title compound (3) was obtained. $^1$H-NMR using a chiral solvating agent confirmed the presence of a single isomer. The absolute configuration was confirmed by derivatization to a compound having known stereochemistry. $^1$H-NMR ($CDCl_3$): δ 1.18 (d, J=7.0 Hz, 3H), 1.16 (d, J=7.6 Hz, 3H), 1.50 (d, J=5.6 Hz, 3H), 2.34 (s, 3H), 2.55 (septet, J=7.2 Hz, 1H), 6.92 (q, J=5.6 Hz, 1H) ppm. $^1$H-NMR with chiral solvating agent (R)-(−)-2,2,2-trifluoro-1-(9-anthryl)ethanol: δ 1.18 (m, 6H), 1.49 (d, J=5.2 Hz, 1.5H), 1.5 (d, J=5.6 Hz, 1.5H), 2.33 (s, 1.5H), 2.34 (s, 1.5H), 2.55 (septet, J=7.2 Hz, 0.5H), 2.56 (septet, J=7.2 Hz, 0.5H), 6.92 (q, J=5.6 Hz, 0.5H), 6.921 (q, J=5.6 Hz, 0.5H) ppm.

Example 4

(1R)-2-Methyl-1-methylthiocarbonyloxypropyl 2-methylpropanoate (4)

A mixture of 2-methyl-1-methylthiocarbonyloxypropyl 2-methylpropanoate (2b) (125 g) and lipase from *Candida rugosa* (Sigma-Aldrich) (12.5 g) in pH 7.2 phosphate buffered saline (1 L) was stirred at room temperature. The reaction was monitored by $^1$H-NMR using the chiral solvating agent (R)-(−)-2,2,2-trifluoro-1-(9-anthryl)ethanol. The reaction was stirred overnight. The reaction mixture was then diluted with ether, and the ether layer separated and filtered through a pad of CELITE® 545 to remove the enzyme. The ether layer was washed with aqueous sodium bicarbonate ($NaHCO_3$) (5 times) and brine, and dried over anhydrous sodium sulfate ($Na_2SO_4$). After rotary evaporation to remove the solvent, 30.4 g of the title compound (4) was obtained. $^1$H-NMR using a chiral solvating agent confirmed the presence of a single isomer. The absolute configuration was determined by derivatization to a compound having known stereochemistry. $^1$H-NMR ($CDCl_3$): δ 0.96 (d, J=6.8 Hz, 6H), 1.16 (d, J=6.8 Hz, 3H), 1.17 (d, J=6.8 Hz, 3H), 1.98-2.07 (m, 1H), 2.32 (s, 3H), 2.56 (septet, J=7.2 Hz, 1H), 6.67 (d, J=5.6 Hz, 1H) ppm.

Example 5

(1R)-1-Methylthiocarbonyloxyethyl benzoate (5)

A mixture of 1-methylthiocarbonyloxyethyl benzoate (2g) (50 g) and lipase from *Candida rugosa* (2.50 g) in pH 7.2 phosphate buffered saline (500 mL) was stirred at room temperature. The reaction was monitored by $^1$H-NMR using the chiral solvating agent (R)-(−)-2,2,2-trifluoro-1-(9-anthryl)ethanol. The reaction was complete after ca. 12 hours. The reaction mixture was diluted with ether and the ether layer separated and filtered through a pad of CELITE® 545 to remove the enzyme. The ether layer was washed with aqueous sodium bicarbonate ($NaHCO_3$) (5 times) and brine, and dried over anhydrous sodium sulfate ($Na_2SO_4$). After the solvent was removed by rotary evaporation, 22 g of the title compound (5) was obtained. $^1$H-NMR using a chiral solvating agent showed a single isomer and the absolute configuration was confirmed by derivatization to a compound having a known stereochemistry. $^1$H-NMR ($CDCl_3$): δ 1.65 (d, J=5.6 Hz, 3H), 2.35 (s, 3H), 7.20 (q, J=5.6 Hz, 1H), 7.45 (m, 2H), 7.58 (m, 1H), 8.06 (m, 2H) ppm.

Example 6

(1S)-Methylthiocarbonyloxyethyl benzoate (6)

A mixture of 1-methylthiocarbonyloxyethyl benzoate (2g) (38 g) and lipase acrylic resin containing *Candida antarctica* lipase B (NOVOZYME® 435, Sigma-Aldrich) (3.8 g) in pH 7.2 phosphate buffered saline (1.6 L) was stirred at room temperature. The reaction was monitored by $^1$H-NMR using the chiral solvating agent (R)-(−)-2,2,2-trifluoro-1-(9-anthryl)ethanol. The reaction was complete in ca. 10 days. The reaction mixture was then diluted with ether, and the ether layer separated and filtered through a pad of CELITE® 545 to remove the enzyme. The ether supernatant was washed with water (5 times) and brine, and dried over anhydrous sodium sulfate ($Na_2SO_4$). After the solvent was removed by rotary evaporation, 15.1 g of the title compound (6) was obtained. $^1$H-NMR using a chiral solvating agent showed a single isomer and the absolute configuration was confirmed by derivatization to a compound having a known stereochemistry.

Example 7

(1R)-2-Methyl-1-methylthiocarbonyloxypropyl butanoate (7)

To a solution of 2-methyl-1-methylthiocarbonyloxypropyl butanoate (2d) (0.5 g) in 2 mL of diisopropyl ether, 0.025 g of lipase from *Candida rugosa* was added, followed by 10 mL of phosphate buffer. The mixture was stirred at room temperature for ca. 24 hrs. The reaction mixture was diluted with ether and the organic solution filtered through a pad of CELITE® 545. The ether solution was washed with water (2 times) and brine, and dried over anhydrous sodium sulfate ($Na_2SO_4$). The solvent was evaporated under reduced pressure to provide 0.16 g (64% yield) of the title compound (7). $^1$H-NMR using a chiral solvating agent showed a single isomer and the absolute configuration was confirmed by derivatization to a compound having a known stereochemistry.

Example 8

(1R)-1-Methylthiocarbonyloxybutyl 2-methylpropanoate (8)

A mixture of methylthiocarbonyloxybutyl 2-methylpropanoate (2c) (0.5 g) and *Candida cylindracea* (Sigma-Aldrich) (0.025 g) in 2 mL of diisopropylether and 10 mL of pH 7.2 phosphate buffer was shaken for ca. 24 hrs at room temperature. The reaction mixture was diluted with diisopropylether and filtered through a CELITE® 545 pad. The organic solution washed with water (2 times) and brine, and dried over anhydrous sodium sulfate (Na$_2$SO$_4$). Following removal of the solvent by rotary evaporation, 0.147 g of the title compound (8) was obtained. $^1$H-NMR using a chiral solvating agent showed a single isomer and the absolute configuration was confirmed by derivatization to a compound having a known stereochemistry.

Example 9

(1R)-Methylthiocarbonyloxybutyl butanoate (9)

A mixture of 1-methylthiocarbonyloxybutyl butanoate (2e) (0.5 g) and *Candida antarctica* lipase B (NOVOZYME® 435) (75 mg) in 2 mL of isopropyl ether and 20 mL of pH 7.2 phosphate buffer was shaken on an orbital shaker at room temperature. The reaction was monitored by $^1$H-NMR using the chiral solvating agent ((R)-(-)-2,2,2-trifluoro-1-(9-anthryl)ethanol. After 24 hours, the reaction was diluted with diisopropylether and filtered through a pad of CELITE® 545. The ether layer was washed with water and brine, and dried with anhydrous sodium sulfate (Na$_2$SO$_4$). Following rotary evaporation to remove the solvent, 0.21 g of the title compound (9) was obtained. Chiral HPLC indicated an enantiomeric excess of 99% e.e. The absolute configuration was confirmed by derivatization to a compound having a known stereochemistry.

Example 10

(1R or 1S)-2-Methyl-1-methylthiocarbonyloxypropyl benzoate (10)

A mixture of 2-methyl-1-methylthiocarbonyloxypropyl benzoate (2h) (7 g) and *Candida rugosa* (0.7 g) in a solvent (10 mL of isopropyl ether and 80 mL of pH 7.2 phosphate buffer saline) was shaken on an orbital shaker at room temperature. The reaction was monitored by $^1$H-NMR with chiral solvating agent. After ca. 7 days, $^1$H-NMR showed that only one isomer remained. The reaction mixture was diluted with ether and ether layer was separated. The ether layer was filtered through a pad of CELITE® 545, washed with water and brine, and dried with anhydrous sodium sulfate (Na$_2$SO$_4$). Rotary evaporation afforded 1.48 g of the title compound as colorless oil. The stereochemistry was not confirmed for this compound.

Example 11

(1R)-2-Methyl-1-methylthiocarbonyloxypropyl Acetate (11)

Following the procedure of Example 9, and substituting 2-methyl-1-methylthiocarbonyloxypropyl acetate (2f) for 1-methylthiocarbonyloxybutyl butanoate (2e), the title compound (11) was obtained (54% yield) with an enantiomeric excess of 94% e.e.

Description 3

Preparation of PLE/MPEG

To a solution of porcine liver esterase (PLE) (Sigma-Aldrich, 7.5 g) in 2,000 mL of water was added poly(ethylene glycol)monomethyl ether (MPEG) (Scientific Polymer Products, Inc., 5000 Mw). The resulting mixture was stirred until a clear solution was obtained. One-hundred (100) mL of acetonitrile was added to the solution to prevent glassware breakage during lyophilization. The mixture was stirred for another 30 min to form a clear solution. The solution was then lyophilized to afford PLE/MPEG (50 mg/1 g) as a fluffy, white powder.

Example 12

(1S)-2-Methyl-1-methylthiocarbonyloxypropyl 2-methylpropanoate (12)

A mixture of 990 mL methyl-tert-butylether (MTBE) and 10 mL water was stirred until a clear solution was obtained (ca. 5 hrs). To this solution was added 2-methyl-1-methylthiocarbonyloxypropyl 2-methylpropanoate (2b) (50 g) and PLE/MPEG (50 mg/1 g, 7.5 g). The resulting suspension was stirred at room temperature. The reaction was monitored by $^1$H-NMR using a chiral solvating agent. After $^1$H-NMR showed only one enantiomer remained in the reaction mixture (ca. 48 hrs), the reaction was quenched by filtration through a pad of CELITE® 545. The supernatant was washed with water, aqueous sodium bicarbonate (NaHCO$_3$) and brine, and dried over anhydrous sodium sulfate (Na$_2$SO$_4$). After rotary evaporation, the title compound (12) was obtained with 70% yield. The enantiomeric excess of the S-enantiomer was 100% e.e. as determined by chiral HPLC. $^1$H-NMR (CDCl$_3$): δ 0.96 (d, J=6.8 Hz, 6H), 1.16 (d, J=6.8 Hz, 3H), 1.17 (d, J=6.8 Hz, 3H), 1.98-2.07 (m, 1H), 2.32 (s, 3H), 2.56 (septet, J=7.2 Hz, 1H), 6.67 (d, J=5.6 Hz, 1H) ppm. $^1$H-NMR with chiral solvating agent (R)-(-)-2,2,2-trifluoro-1-(9-anthryl)ethanol: δ 0.98 (d, J=6.8 Hz, 3H), 0.99 (d, J=6.8 Hz, 3H), 1.19 (d, J=7.2 Hz, 1.5H), 1.19 (d, J=6.8 Hz, 1.5H), 1.20 (d, J=6.8 Hz, 1.5H), 1.20 (d, J=7.2 Hz, 1.5H), 2.01-2.09 (m, 1H), 2.34 1(s, 1.5H), 2.44 (s, 1.5H), 2.59 (septet, J=7.2 Hz, 0.5H), 2.59 (septet, J=6.8 Hz, 0.5H), 6.70 (d, J=5.6 Hz, 0.5H), 6.70 (d, J=5.2 Hz, 0.5H) ppm.

Example 13

Alternate Synthesis of (1S)-2-Methyl-1-methylthiocarbonyloxypropyl-2-methylpropanoate (13)

2-Methyl-1-methylthiocarbonyloxypropyl 2-methylpropanoate (2b) (119 mg) in 100 µL 0.4 M phosphate buffer (pH 7.5) and *Candida antarctica* lipase A (4-6µL, NOVOZYME® 735, 6 units/mg) were added to 500 µL phosphate buffer (0.4-0.8 M, pH 7.5) and shaken on an Eppendorf thermomixer at 1,000 rpm at a temperature of 29° C. After ca. 43 hours, chiral HPLC analysis indicated an enantiomeric excess of 99% e.e. for the title compound (13).

Example 14

(1S)-2-Methyl-1-methylthiocarbonyloxypropyl butanoate (14)

2-Methyl-1-methylthiocarbonyloxypropyl butanoate (2d) (1 g) was dissolved in 20 mL of MTBE, saturated with 1% of water, 1.3 g of PLE/MPEG (7.5%, 60 mg/1 g) was added, and the mixture shaken at room temperature for 24 hrs. Hexane was added to the reaction mixture and after filtration through a CELITE® 545 pad, the organic solution was washed with water, aqueous sodium bicarbonate (NaHCO$_3$) and brine, and dried over anhydrous sodium sulfate (Na$_2$SO$_4$). After evaporating the solvent under reduced pressure the title compound

(14) was obtained (0.29 g, 58% yield). The absolute configuration was determined by derivatization to a compound having known stereochemistry.

Example 15

(1S)-1-Methylthiocarbonyloxybutyl 2-methylpropanoate (15)

A mixture of 22 mL methyl-tert-butyl ether (MTBE) and 0.22 mL water was stirred until a clear solution was obtained (ca. 5 hrs). To this solution was added methylthiocarbonyloxybutyl 2-methylpropanoate (2c) (1.11 g) and PLE/MPEG (50 mg/1 g, 1.5 g). The resulting suspension was stirred at room temperature. The reaction was monitored by $^1$H-NMR using a chiral solvating agent. After ca. 5 days, the reaction was quenched by filtration through a pad of CELITE® 545. The supernatant was washed with water, aqueous sodium bicarbonate (NaHCO$_3$) and brine, and dried over anhydrous sodium sulfate (Na$_2$SO$_4$). Rotary evaporation of the solvent afforded 0.22 g the title compound (15) (40% yield). The enantiomeric excess was 88% e.e. as determined by chiral HPLC.

Example 16

(1S)-1-Methylthiocarbonyloxybutyl butanoate (16)

A mixture of 33 mL methyl-tert-butyl ether (MTBE) and 0.33 mL water was stirred until a clear solution was obtained (ca. 5 hrs). To this solution was added methylthiocarbonyloxybutyl butanoate (2e) (2.0 g) and PLE/MPEG (60 mg/1 g; 12.65 g). The resulting suspension was stirred at room temperature. The reaction was monitored by $^1$H-NMR using a chiral solvating agent. After ca. 5 days, the reaction was quenched by filtration through a pad of CELITE® 545. The supernatant was washed with water, aqueous sodium bicarbonate (NaHCO$_3$) and brine, and dried over anhydrous sodium sulfate (Na$_2$SO$_4$). Evaporation of the solvent afforded 0.20 g (20% yield) of the title compound (16). The enantiomeric excess as determined by chiral HPLC was 90% e.e.

Example 17

(1S)-2-Methyl-1-methylthiocarbonyloxypropyl acetate (17)

Twenty (20) mL of methyl-tert-butyl ether (MTBE) and 0.2 mL of water were shaken for 4 hrs until the solution was clear at which time 1 g of 2-methyl-1-methylthiocarbonyloxypropyl acetate (2f) was added, followed by 1.32 g of PLE/MPEG (60 mg/1 g). The mixture was shaken on an orbital shaker for 7 hrs. Hexane was added and the mixture was filtered through CELITE® 545 pad. The organic solution was washed with water, aqueous sodium bicarbonate (NaHCO$_3$) solution and brine, and dried over anhydrous sodium sulfate (Na$_2$SO$_4$). After evaporation of solvent, 0.32 g (64% yield) of the title compound (17) was obtained having an enantiomeric excess of 64% e.e. The absolute configuration was determined by independent stereospecific synthesis and by derivatization to a compound having known stereochemistry.

Example 18

(3S)-{[(1R)-Isobutanoyloxyethoxy]carbonylaminomethyl}-5-methyl-hexanoic Acid (18)

Step A: (1R)-1-Methylthiocarbonyloxyethyl-2-methylpropanoate (3)

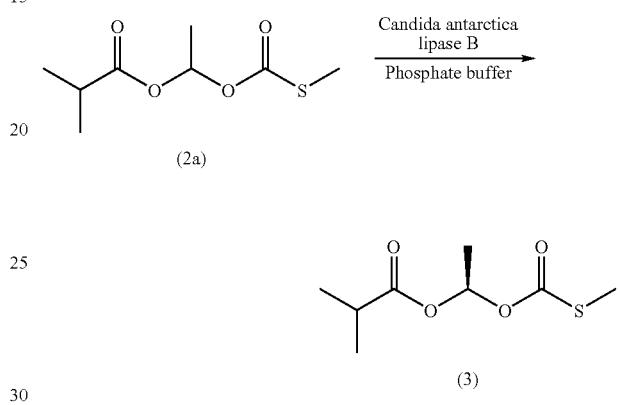

A 20-L, multi-necked, cylindrical reactor, fitted with a mechanical stirrer, a nitrogen inlet and an outlet connected to an oxidation bath and a bleach bath (14% NaOCl) to oxidize librated methanethiol and acetaldehyde was charged with racemic 1-methylthiocarbonyloxyethyl-2-methylpropanoate (2a) (5.32 kg, 25.8 mol) and 0.8 M phosphate buffer (10 L, pH 7.0). Solid supported *Candida antarctica* lipase B (125 g, NOVOZYME® 435) was slowly added while the solution was stirred. The reaction mixture was stirred at room temperature (22-24° C.) for ca. 18 hours.

The reaction mixture was then diluted with methyl tert-butyl ether (MTBE) (8 L) and the organic phase separated. The organic phase was washed with phosphate buffer (0.57 M, 2×5 L), water (10 L) and brine (7 L). The solid supported enzyme was removed by filtration and the organic phase was dried over sodium sulfate (Na$_2$SO$_4$), filtered and concentrated by rotary evaporation to afford the title compound (3) as a light yellow oil. The product was further concentrated at 65° C. under reduced pressure to provide 2.45 kg of the title compound (3) (92% yield). $^1$H-NMR (CDCl$_3$): δ 1.17 (d, J=7.0 Hz, 3H), 1.18 (d, J=7.6 Hz, 3H), 1.59 (d, J=5.6 Hz, 3H), 2.34 (s, 3H), 2.55 (septet, J=7.2 Hz, 1H), 6.92 (q, J=5.6 Hz, 1H) ppm. $^1$H-NMR in presence of (R)-(−)-2,2,2-trifluoro-1-(9-anthryl)ethanol as chiral solvating agent (CDCl$_3$): δ 1.17 (d, J=7.2 Hz, 3H), 1.18 (d, J=7.2 Hz, 3H), 1.48 (d, J=5.6 Hz, 3H), 2.33 (s, 3H), 2.56 (septet, J=7.2 Hz, 1H), 6.92 (q, J=5.6 Hz, 1H) ppm.

For comparison, racemic 1-methylthiocarbonyloxyethyl-2-methylpropanoate: $^1$H-NMR in presence of (R)-(−)-2,2,2-trifluoro-1-(9-anthryl)ethanol as chiral solvating agent (CDCl$_3$): δ 1.18 (m, 6H), 1.49 (d, J=5.2 Hz, 1.5H), 1.50 (d, J=5.6 Hz, 1.5H), 2.33 (s, 1.5H), 2.34 (s, 1.5H), 2.55 (septet, J=7.2 Hz, 0.5H), 2.56 (septet, J=7.2 Hz, 0.5H), 6.92 (q, J=5.6 Hz, 0.5H), 6.92 (q, J=5.6 Hz, 0.5H) ppm.

Step B: {[(1R)-Isobutanoyloxyethoxy]carbonyloxy} succinimide (18b)

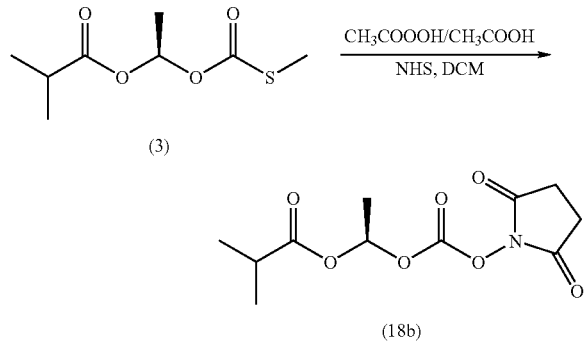

In a 20-L jacketed reaction vessel equipped with a mechanical stirrer, an internal thermometer and a nitrogen inlet was added (1R)-1-methylthiocarbonyloxyethyl-2-methylpropanoate (3) (1.44 kg, 7 mol), and N-hydroxysuccinimide (1.61 kg, 14 mol) in dichloromethane (DCM) (8 L). The resulting suspension was cooled to 9° C. A solution of peracetic acid in acetic acid (32%, 4.98 kg, 4.4 L; 21 mol) was slowly added while maintaining the reaction temperature between 9° C. and 15° C. The reaction mixture was then stirred at 9° C. for ca. 23 hours.

The reaction mixture was then diluted with water (3 L) and the organic phase was separated. The organic phase was washed with water (2×2 L), saturated potassium bicarbonate solution (4 L) and a solution of sodium thiosulfate (350 g in water 4 L). The organic phase was dried over sodium sulfate (Na$_2$SO$_4$) and volatiles were removed under vacuum, resulting in the crude product as a white-solid. To this solid was added 2-propanol (3 L) and hexane (3 L). The resulting slurry was warmed to 30° C. for 30 minutes. The resulting slurry was cooled for two hours using an ice-bath. The product was collected by filtration. The filter cake was washed with hexane (4 L) and dried under vacuum to provide the title compound (18b) as a white solid (1 kg, 50% yield). $^1$H-NMR (CDCl$_3$): 1.17 (d, J=6.8 Hz, 3H), 1.18 (d, J=6.8 Hz, 3H), 1.60 (d, J=5.6 Hz, 3H), 2.58 (m, 1H), 2.83 (s, 4H), 6.80 (q, J=5.2 Hz, 1H) ppm.

Step C: (3S)-{[(1R)-Isobutanoyloxyethoxy]carbonylaminomethyl}-5-methyl-hexanoic Acid (18)

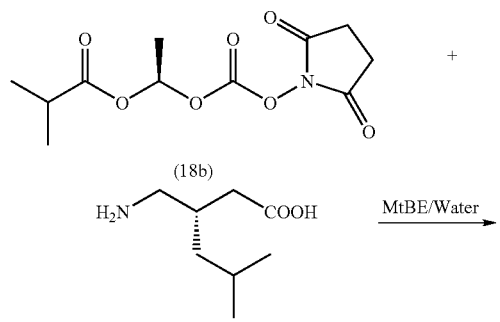

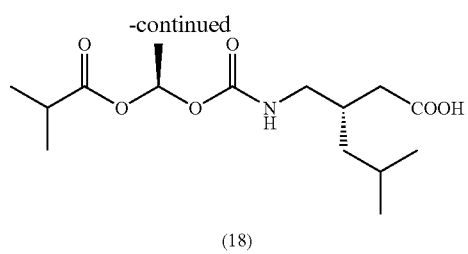

A 20-L pilot plant equipped with a mechanical stirrer and a nitrogen inlet was charged with NHS-carbonate, {[(1R) Isobutanoyloxyethoxy]carbonyloxy} succinimide (18b), 1.31 kg, 4.7 mol) and (S)-pregabalin (431 g; overall 1.2 eq. of pregabalin) in a mixture of methyl tert-butyl ether (MTBE) and water (3:1; 10 L). The resulting suspension was stirred for 24 hours at room temperature.

The reaction mixture was then diluted with water (3 L). The organic phase was separated and washed with water (3×3 L), aqueous sulfuric acid (5%, 4 L), and water (4 L). The organic phase was dried over sodium sulfate (Na$_2$SO$_4$) and volatiles were removed under vacuum to provide the title compound (18) as a clear, viscous-oil (1.33 kg, 89% yield).

Example 19

Alternate Synthesis of (3S)-{[(1R)-Isobutanoyloxyethoxy]carbonylaminomethyl}-5-methyl-hexanoic Acid (18)

Step A: (1R)-Methylthiocarbonyloxyethyl 2-methylpropanoate (3)

Methylthiocarbonyloxyethyl-2-methylpropanoate (180 g), prepared as described in Gallop et al., U.S. Pat. No. 7,227,028, and lipase from *Candida antarctica* lipase B (NOVOZYME® 435), immobilized on acrylic resin, (8.0 g) was stirred in phosphate buffered saline, pH 7.2, (1.6 L) at room temperature. The progress of the reaction was monitored by $^1$H-NMR using the chiral solvating agent (R)-(+)-2,2,2-trifluoro-1-(9-anthryl)ethanol and was complete within ca. 16 h. The reaction mixture was diluted with ether and the ether layer separated and filtered through a pad of CELITE® to remove the enzyme. The ether phase was washed repeatedly with water then brine, and dried over anhydrous sodium sulfate (Na$_2$SO$_4$). Removal of the solvent in vacuo afforded a quantitative yield (90 g) of the title compound (3) as a single enantiomer. The absolute configuration was established by: (i) conversion to compound (18b) (see Step B); (ii) reaction of (18b) with gabapentin to afford 1-{[(α-(R)-isobutanoyloxyethoxy)carbonyl]aminomethyl}-1-cyclohexane acetic acid; and (iii) correlation with the product formed by stereoselective Baeyer-Villiger oxidation of 1-{[(α-(R)-isobutanoylethoxy)carbonyl]aminomethyl}-1-cyclohexane acetic acid as described in Gallop et al., U.S. Pat. No. 6,927,036. $^1$H NMR (CDCl$_3$, 400 MHz): δ 1.16 (d, J=7.6 Hz, 3H), 1.18 (d, J=7.0 Hz, 3H), 1.50 (d, J=5.6 Hz, 3H), 2.34 (s, 3H), 2.55 (hept, J=7.2 Hz, 1H), 6.92 (q, J=5.6 Hz, 1H) ppm. $^1$H NMR in presence of chiral solvating agent, (R)-(-)-2,2,2-trifluoro-1-(9-anthryl)ethanol: δ 1.18 (m, 6H), 1.50 (d, J=5.2 Hz, 1.5H), 1.50 (d, J=5.6 Hz, 1.5H), 2.33 (s, 1.5H), 2.34 (s, 1.5H), 2.55 (septet, J=7.2 Hz, 0.5H), 2.56 (septet, J=7.2 Hz, 0.5H), 6.92 (q, J=5.6 Hz, 0.5H), 6.92 (q, J=5.6 Hz, 0.5H) ppm.

Step B: {[(1R)-Isobutanoyloxyethoxy]carbonyloxy} succinimide (18b)

The title compound (18b) was prepared from compound (1R)-methylthiocarbonyloxyethyl 2-methylpropanoate (3)

by following the method disclosed in Example 10 of Gallop et al., U.S. Pat. No. 7,227,028. $^1$H NMR (CDCl$_3$, 400 MHz): δ 1.17 (d, J=6.8 Hz, 6H), 1.56 (d, J=5.6 Hz, 3H), 2.55 (m, 1H), 2.82 (s, 4H), 6.80 (q, J=5.2 Hz, 1H) ppm.

Step C: (3S)-{[(1R)-Isobutanoyloxyethoxy]carbonylaminomethyl}-5-methyl-hexanoic Acid (18)

Compound (18b) (52.8 g, 0.193 mol) and pregabalin (31.7 g, 0.199 mol) were stirred in a mixture of acetonitrile and water (200 mL, 4:1) at room temperature for 16 h, and the acetonitrile removed in vacuo. The residue was partitioned between MTBE and water, the MTBE layer was then washed with water then brine, and dried over anhydrous sodium sulfate (Na$_2$SO$_4$). Removing the solvent in vacuo afforded the title compound (18) (61.3 g, 100% yield) as a colorless oil. $^1$H NMR (CDCl$_3$, 400 MHz): δ 0.90 (d, J=6.4 Hz, 3H), 0.92 (d, J=6.4 Hz, 3H), 1.17 (m, 8H), 1.47 (d, J=5.6 Hz, 2.7H), 1.50 (d, J=5.6 Hz, 0.3H), 1.66 (hept, J=6.8 Hz, 1H), 2.19 (m, 1H), 2.27 (dd, J=15.2, 7.6 Hz, 1H), 2.37 (dd, J=15.2, 5.2 Hz, 1H), 2.54 (hept, J=6.8 Hz, 1H), 3.08 (m, 1H), 3.32 (m, 1H), 5.00 (br, t, J=6.2 Hz, 0.9H), 5.91 (br, t, J=6.2 Hz, 0.1H), 6.76 (q, J=5.6 Hz, 1H) ppm.

Example 20

(3S)-{[(1S)-Isobutanoyloxyisobutoxy]carbonylaminomethyl}-5-methyl-hexanoic Acid (20)

Step A: (1S)-2-Methyl-1-methylthiocarbonyloxypropyl 2-methylpropanoate (12)

A mixture of MTBE (990 mL) and water (10 mL) was stirred for 5 h until a clear solution was obtained. To this solution was added 2-methyl-1-methylthiocarbonyloxypropyl 2-methylpropanoate (2b) (50 g), prepared as described in Gallop et al., U.S. Pat. No. 7,227,028, and a non-covalent complex of porcine liver esterase (PLE), with methoxypolyethylene glycol (mPEG) (5 wt %, 75 g) prepared according to the method described by Heiss and Gais, *Tetrahedron Lett.*, 1995, 36, 3833-3836; and Rupport and Gais, *Tetrahedron Asymmetry*, 1997, 8(21), 3657-3664. The resulting suspension was stirred at room temperature and the reaction periodically monitored by $^1$H-NMR using the chiral solvating agent (R)-(+)-2,2,2-trifluoro-1-(9-anthryl)ethanol. After ca. 48 h, $^1$H-NMR indicated that only one enantiomer remained in the reaction mixture at which time the reaction was quenched by filtration through a pad of CELITE®. The supernatant was washed with water, aqueous sodium bicarbonate (NaHCO$_3$) then brine, and dried over anhydrous sodium sulfate (Na$_2$SO$_4$). After removing the solvent in vacuo, the title compound (12) was isolated as a single S-enantiomer (as determined by HPLC using a chiral column) in 70% yield. The absolute configuration was established by: (i) conversion to compound (20b) (see Step B); (ii) reaction of (20b) with R-baclofen to afford 4-{[(1S)-isobutanoyloxyisobutoxy]carbonylamino}-(3R)-(4-chlorophenyl)-butanoic acid; and (iii) correlation with the product formed in Example 18 of Gallop et al., U.S. Pat. No. 7,227,028. $^1$H NMR (CDCl$_3$, 400 MHz): δ 0.96 (d, J=6.8 Hz, 6H), 1.16 (d, J=6.8 Hz, 3H), 1.17 (d, J=6.8 Hz, 3H), 1.98-2.07 (m, 1H), 2.32 (s, 3H), 2.56 (hept, J=7.2 Hz, 1H), 6.67 (d, J=5.6 Hz, 1H). $^1$H NMR with chiral solvating agent, (R)-(−)-2,2,2-trifluoro-1-(9-anthryl)ethanol: δ 0.98 (d, J=6.8Hz, 3H), 0.99 (d, J=6.8 Hz, 3H), 1.19 (d, J=7.2 Hz, 1.5H), 1.19 (d, J=6.8 Hz, 1.5H), 1.20 (d, J=6.8 Hz, 1.5H), 1.20 (d, J=7.2 Hz, 1.5H), 2.01-2.09 (m, 1H), 2.34 (s, 1.5H), 2.444 (s, 1.5H), 2.591 (hept, J=7.2 Hz, 0.5H), 2.59 (hept, J=6.8 Hz, 0.5H), 6.70 (d, J=5.6 Hz, 0.5H), 6.70 (d, J=5.2 Hz, 0.5H).

Step B: {[(1S)-Isobutanoyloxyisobutoxy]carbonyloxy} succinimide (20b)

The title compound (20b) was prepared from compound (12) by following the method disclosed in Example 10 of Gallop et al., U.S. Pat. No. 7,227,028.

Step C: (3S)-{[(1S)-Isobutanoyloxyisobutoxy]carbonylaminomethyl}-5-methyl-hexanoic Acid (20)

Compound (20b) (10.21 g, 33.9 mmol) and pregabalin (5.5 g, 34.6 mmol) were stirred in a mixture of acetonitrile and water (60 mL, 4:1) for 6 h at room temperature, and then the acetonitrile was removed in vacuo. The residue was partitioned between MTBE and water, the MTBE layer washed repeatedly with water then brine, and dried over anhydrous sodium sulfate (Na$_2$SO$_4$). Removing the solvent in vacuo afforded the title compound (20) as a colorless oil (11.65 g, 100% yield). $^1$H NMR (CDCl$_3$, 400 MHz): δ 0.90 (t, J=6.8 Hz, 6H), 0.97 (J=6.8 Hz, 6H), 1.18 (d, J=6.8 Hz, 3H), 1.18 (d, J=7.2 Hz, 3H), 1.19 (m, 2H), 1.67 (hept, J=6.8 Hz, 1H), 2.03 (m, 1H), 2.12 (m, 1H), 2.07 (m, 2H), 2.56 (hept, J=7.2 Hz, 1H), 3.17 (m, 1H), 3.29 (m, 1H), 4.95 (br.t, J=6.0 Hz, 0.83H), 5.74 (br. t, J=6.0 Hz, 0.17H), 6.55 (d, J=5.2 Hz, 0.83H), 6.61 (br.d, J=4.4 Hz, 0.17H).

Example 21

(3S)-{[(1R)-Benzoyloxyethoxy]carbonylaminomethyl}-5-methyl-hexanoic Acid (21)

Step A: (1R)-1-Methylthiocarbonyloxyethyl benzoate (5)

1-Methylthiocarbonyloxyethyl benzoate (2g) (50 g), prepared as described in Gallop et al., U.S. Pat. No. 7,227,028, and lipase from *Candida rugosa* (2.5 g) were stirred in phosphate buffered saline, pH 7.2, (0.5 L) at room temperature. The progress of the reaction was monitored by $^1$H-NMR using the chiral solvating agent [(R)-(+)-2,2,2-trifluoro-1-(9-anthryl)ethanol] and was complete within 16 h. The reaction mixture was diluted with ether and the ether layer separated and filtered through a pad of CELITE® to remove the enzyme. The ether phase was washed repeatedly with aqueous sodium bicarbonate then brine, and dried over anhydrous sodium sulfate (Na$_2$SO$_4$). Removing the solvent in vacuo afforded 22 g of the title compound (5) as a single enantiomer. $^1$H NMR (CDCl$_3$, 400 MHz): δ 1.65 (d, J=5.6 Hz, 3H), 2.35 (s, 3H), 7.20 (q, J=5.6 Hz, 1H), 7.45 (m, 2H), 7.58 (m, 1H), 8.06 (m, 2H) ppm.

Step B: {[(1R)-Benzoyloxyethoxy]carbonyloxy} succinimide (21b)

The title compound (21b) was prepared from compound (5) by following the method disclosed in Example 10 of Gallop et al., U.S. Pat. No. 7,227,028. $^1$H NMR (CDCl$_3$, 400 MHz): δ 1.75 (d, J=5.6 Hz, 3H), 2.82 (s, 4H), 7.07 (q, J=5.4 Hz, 1H), 7.45 (m, 2H), 7.59 (m, 1H), 8.05 (m, 2H) ppm.

Step C: (3S)-{[(1R)-Benzoyloxyethoxy]carbonylaminomethyl}-5-methyl-hexanoic Acid (21)

Compound (21b) (25.5 g, 83.1 mmol) and pregabalin (13.6 g, 85.4 mmol) were stirred in a mixture of acetonitrile and water (100 mL, 4:1) for 16 h at room temperature, and then the acetonitrile was removed in vacuo. The residue was partitioned between MTBE and water, the MTBE layer washed repeatedly with water then brine, and then dried over anhydrous sodium sulfate (Na$_2$SO$_4$). Removing the solvent in vacuo afforded the title compound (21) as a colorless oil (29.09 g, 100% yield). $^1$H NMR (CDCl$_3$, 400 MHz): δ 0.88 (t, J=6.8 Hz, 6H), 1.17 (m, 2H), 1.60 (d, J=5.2 Hz, 3H), 1.64 (m, 1H), 2.17 (m, 1H), 2.27 (dd, J=7.6, 15.2 Hz, 1H), 2.35 (dd, J=15.2, 5.6 Hz, 1H), 3.11 (m, 1H), 3.28 (m, 1H), 5.06 (br, t, J=6.4 Hz, 0.83H), 5.97 (br, t, J=6.4 Hz, 0.13H), 7.03 (m, 1H), 7.41 (m, 2H), 7.54 (m, 1H), 8.03 (m, 2H) ppm.

Example 22

(3R)-4-{[(1S)-2-Methyl-1-(2-methylpropanoyloxy)propoxy]carbonylamino}-3-(4-chlorophenyl)butanoic Acid (22)

The title compound (22) may be synthesized by adapting the procedures described in Example 17.

Step A: (1S)-1-Methylthiocarbonyloxyethyl-2-methylpropanoate (12)

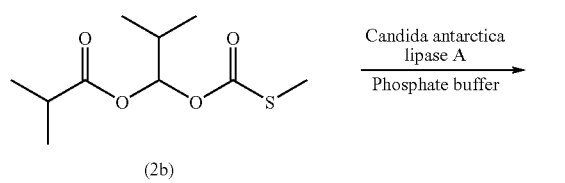

(2b)

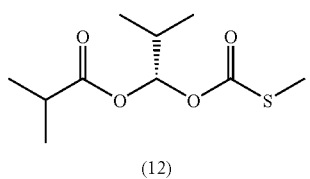

(12)

A 20-L, multi-necked, cylindrical reactor, fitted with a mechanical stirrer, a nitrogen inlet and an outlet connected to an oxidation bath, and a bleach bath (14% NaOCl) to oxidize librated methanethiol and acetaldehyde is charged with racemic 2-methyl-1-methylthiocarbonyloxypropyl 2-methylpropanoate (2b) (5.32 kg, 25.8 mol) and 0.8 M phosphate buffer (10 L, pH 7.0). Solid supported *Candida antarctica* lipase A (125 g, NOVOZYME® 735, NOVOZYME®; CHIRAZYME™ L-5, Roche Diagnostics; or other suppliers) is slowly added while stirred. The reaction mixture is stirred at room temperature (22-24° C.) for ca. 18 hours.

The reaction mixture is diluted with methyl tert-butyl ether (MTBE) or alternatively dichloromethane (DCM) (8 L) and the organic phase separated. The organic phase is washed with phosphate buffer (0.57 M, 2×5 L), water (10 L) and brine (7 L). The solid supported enzyme is removed by filtration and the organic phase is dried over sodium sulfate (Na$_2$SO$_4$), filtered, and concentrated by rotary evaporation to afford the title compound (12).

Step B: {[(1S)-Isobutanoyloxyisobutoxy]carbonyloxy} succinimide (20b)

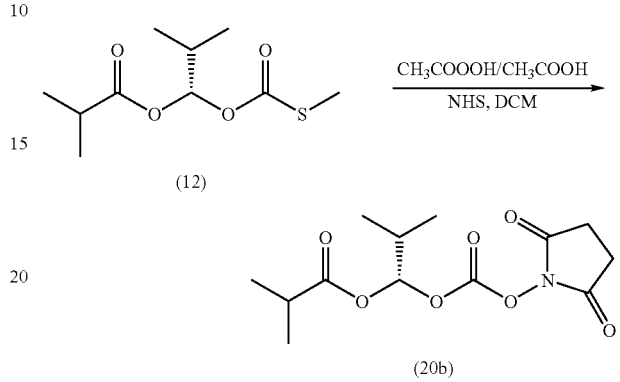

In a 20-L jacketed reaction vessel equipped with a mechanical stirrer, an internal thermometer and a nitrogen inlet is added (1S)-1-methylthiocarbonyloxyethyl-2-methylpropanoate (12) (1.442 kg, 7 mol), and N-hydroxysuccinimide (1.610 kg, 14 mol) in dichloromethane (DCM) (8 L). The resulting suspension is cooled to 9° C. A solution of peracetic acid in acetic acid (32%, 4.98 kg, 4.4 L, 21 mol) is slowly added while maintaining the reaction temperature between 9° C. and 15° C. The reaction mixture is then stirred at 9° C. for 23 hours.

The reaction mixture is then diluted with water (3 L) and the organic phase is separated. The organic phase is washed with water (2×2 L), saturated potassium bicarbonate solution (4 L) and a solution of sodium thiosulfate (350 g in water 4 L). The organic phase is dried over sodium sulfate (Na$_2$SO$_4$) and volatiles are removed under vacuum, resulting in the crude product as a white-solid. To this solid is added 2-propanol (3 L) and hexane (3 L). The resulting slurry is warmed to 30° C. for 30 minutes. The resulting slurry is cooled for two hours using an ice-bath. The product is collected by filtration. The filter cake is washed with hexane (4 L) and dried under vacuum to provide the title compound (20b).

Step C: (3R)-4-{[(1S)-2-Methyl-1-(2-methylpropanoyloxy)propoxy]carbonylamino}-3-(4-chlorophenyl)butanoic Acid (22)

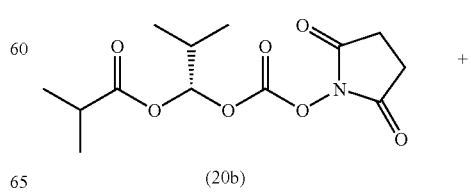

(20b)

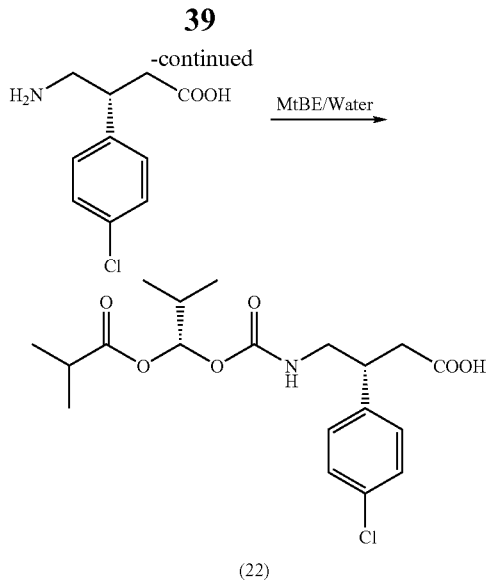

A 20-L pilot plant equipped with a mechanical stirrer and a nitrogen inlet was charged with NHS-carbonate, 1-S-[[[(isobutyryloxy)isobutyroxy]carbonyl]oxy]-2,5-pyrrolidinedione (20b), 1.31 kg, 4.7 mol) and (R)-baclofen (431 g; overall 1.2 eq. of R-baclofen) in a mixture of methyl tert-butyl ether (MTBE) and water (3:1; 10 L). The resulting suspension is stirred for 24 hours at room temperature.

The reaction mixture is then diluted with water (3 L). The organic phase is separated and washed with water (3×3 L), aqueous sulfuric acid (5%, 4 L), and water (4 L). The organic phase is dried over sodium sulfate ($Na_2SO_4$) and volatiles are removed under vacuum to provide the title compound (22).

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of enantiomerically enriching an enantiomeric mixture of a compound of Formula (I), comprising:

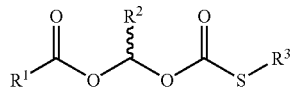

reacting the enantiomeric mixture with an enzyme selected from an esterase, a protease and a lipase to provide an enantiomerically enriched mixture having at least 90% enantiomeric excess of one enantiomer of the compound of Formula (I), wherein:

$R^1$ is chosen from $C_{1-6}$ alkyl, $C_{3-6}$ cycloalkyl, phenyl, substituted phenyl, and $C_{7-9}$ phenylalkyl;

$R^2$ is chosen from $C_{1-4}$ alkyl, $C_{3-6}$ cycloalkyl, phenyl, substituted phenyl, and $C_{7-9}$ phenylalkyl; and $R^3$ is chosen from $C_{1-6}$ alkyl, $C_{3-6}$ cycloalkyl, phenyl, substituted phenyl, and $C_{7-9}$ phenylalkyl.

2. The method of claim 1, wherein the enantiomerically enriched mixture has an enantiomeric excess of the R isomer and the enzyme is a lipase selected from *Candida rugosa* lipase B, *Candida cylindracea* lipase B, and *Candida antarctica* lipase B.

3. The method of claim 1, wherein the enantiomerically enriched mixture has an enantiomeric excess of the S isomer and the enzyme is a lipase selected from *Candida antarctica* lipase A, and *Candida antarctica* lipase B.

4. The method of claim 1, wherein the enzyme is *Candida antarctica* lipase B, $R^1$ is isopropyl, $R^2$ is methyl, $R^3$ is methyl, and the enantiomerically enriched mixture has an enantiomeric excess of the R enantiomer of the compound of Formula (I).

5. The method of claim 1, wherein the enzyme is *Candida antarctica* lipase A, $R^1$ is isopropyl, $R^2$ is isopropyl, $R^3$ is methyl, and the enantiomerically enriched mixture has an enantiomeric excess of the S enantiomer of the compound of Formula (I).

6. The method of claim 1, wherein $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, and cyclohexyl.

7. The method of claim 1, wherein $R^2$ is chosen from methyl, ethyl, n-propyl, isopropyl, n-butyl, isobutyl, sec-butyl, phenyl, and cyclohexyl.

8. The method of claim 1, wherein $R^3$ is methyl.

9. The method of claim 1, wherein:
$R^1$ is chosen from methyl, isopropyl, n-propyl, and phenyl;
$R^2$ is chosen from methyl, isopropyl, and n-propyl; and
$R^3$ is methyl.

10. The method of claim 1, wherein each substituent is independently chosen from halogen, —OH, —CN, —$CF_3$, =O, —$NO_2$, $C_{1-3}$ alkoxy, $C_{1-3}$ alkyl, —$COOR^{15}$ wherein $R^{15}$ is chosen from hydrogen and $C_{1-3}$ alkyl, and —$N(R^{15})_2$ wherein each $R^{15}$ is independently chosen from hydrogen and $C_{1-3}$ alkyl.

11. A method of making an enantiomerically enriched mixture of a compound of Formula (II)

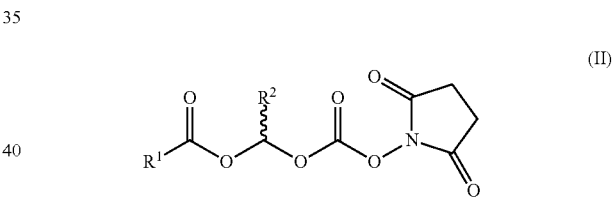

or a salt thereof, comprising:
enantiomerically enriching an enantiomeric mixture of a compound of Formula (I) according to the method of claim 1, and
reacting the enantiomerically enriched mixture having at least 90% enantiomeric excess of one enantiomer of the compound of Formula (I) with N-hydroxysuccinimide to provide the corresponding enantiomerically enriched mixture of the compound of Formula (II) or a salt thereof.

12. A method of making an enantiomerically enriched mixture of a compound of Formula (III)

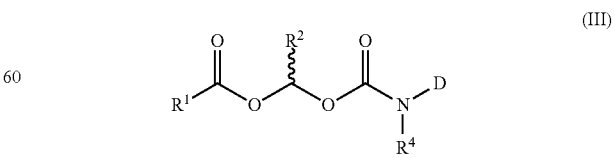

or a salt thereof, comprising: making an enantiomeric mixture of a compound of Formula (II) or a salt thereof according to the method of claim 11, and reacting the enantiomerically enriched mixture of the compound of Formula (II) or a salt thereof with a drug D-NHR$^4$, or a salt thereof, comprising a primary or secondary amine group to provide the corresponding enantiomerically enriched mixture of the compound of Formula (III) or a salt thereof, wherein D-NHR$^4$ is selected from acebutolol, adaprolol, adrenalone, adrogolide, aladapcin, alatrofloxacin, albendazole, albuterol, albutoin, alendronate, alestramustine, aletamine, alinidine, aliskiren, alizapride, alniditan, alprafenone, alprenolol, alprenoxime, altromycin A, altromycin C, amantadine, amidephrine, amifostine, amikacin, amiloride, aminolevulinic acid, aminorex, amlodipine, amosulalol, amoxapine, amphetamine, amphotericin B, amrubicin, amselamine, amthamine, anabasine, angiopeptin, anisperimus, aprinocid, arbekacin, arbutamine, argiopine, arotinolol, aspartame, aspoxicillin, atenolol, avizafone, azoxybacilin, baclofen, R-baclofen, bactobolin, balanol, balofloxacin, bambuterol, bamethan, baogongteng A, barusiban, batoprazine, becampanel, befunolol, belactosin A, belactosin C, benanomicin B, benazepril, berlafenone, betahistine, betaxolol, bevantolol, biemnidin, binospirone, bisoprolol, boholmycin, bopindolol, brasilicardin A, brinzolamide, bunolol, bupropion, butabindide, buteranol, butofilolol, butopamine, butoxamine, caldaret, cambendazole, cambrescidins, caprazamycin, capromorelin, capsavanil, carbidopa, carbuterol, carteolol, carvedilol, cefaclor, cefcanel, cefcanel daloxate, cefminox, cefprozil, ceftizoxime, celiprolol, ceranapril, cetefloxacin, chlorotetain, chlortermine, cilazapril, cimaterol, cimetidine, cinacalcet, ciprofloxacin, circinamide, cisapride, cispentacin, clonidine, cloranolol, clorprenaline, colterol, cyclobendazole, cyclothialidine, cystamine, cystocin, cytaramycin, dabelotine, dactimicin, dalargin, dalbavancin, daunorubicin, D-cycloserine, decaplanin, deferoxamine, delapril, delavirdine, delfaprazine, delucemine, demexiptiline, denopamine, deoxymethylspergualin, deoxynegamycin, deoxynojirimycin, deoxyspergualin, desipramine, desloratadine, deterenol, dexpropranolol, diacetolol, dihydrexidine, dilevalol, dimethoxyphenethylamine, dinapsoline, dirithromycin, dobutamine, donitriptan, dopamine, dopexamine, doripenem, dorzolamide, doxorubicin, droxidopa, droxinavir, duloxetine, duramycin, ecenofloxacin, ecteinascidins, efegatran, eflornithine, eglumegad, elarofiban, enalapril, enalkiren, enkastins, enoxacin, enviroxime, ephrinephrine, epibatidine, epirubicin, epithalon, eremomycin, ersentilide, ertapenem, esafloxacin, esmolol, esperamicin A1, etintidine, etryptamine, examorelin, exaprolol, exatecan, ezlopitant, fasudil, fenbendazole, fenfluramine, fenmetazole, fenoldopam, fenoterol, fenyripol, fepradinol, ferulinolol, flecainide, flubendazole, fludorex, fluoxetine, fluparoxan, fluvirucin B2, fluvoxamine, formoterol, fortimicin A, fosopamine, frovatriptan, fudosteine, gaboxadol, galarubicin, gatnon, garenoxacin, garomefrine, gatifloxacin, gemifloxacin, gilatide, giracodazole, gludopa, halofuginone, helvecardin A, helvecardin B, hispidospermidin, histaprodifen, hydrostatin A, ibopamine, ibutamoren, icadronate, icatibant, icofungipen, idarubicin, imidapril, immepip, immepyr, immucillin-H, impentamine, indeloxazine, inogatran, isodoxorubicin, isofagomine, janthinomycins, kahalalide F, kaitocephalin, kanamycin, ketamine, L-4-oxalysine, labetalol, ladostigil, lagatide, landiolol, lanicemine, lanomycin, lapatinib, lazabemide, L-dopa, lenapenem, lerisetron, leurubicin, leustroducsin A, leustroducsin B, leustroducsin C, leustroducsin H, levobunolol, L-histidinol, L-homothiocitrulline, lisinopril, litoxetine, lobendazole, lobophorin A, loracarbef, lotrafiban, L-thiocitrulline, lubazodone, lysobactin, mabuterol, manzamines, maprotiline, maropitant, mebendazole, mecamylamine, mefloquine, melagatran, meluadrine, memantine, mepindolol, meropenem, mersacidin, metaproterenol, metaraminol, metazoline, methoctramine, methyldopa, methylphenidate, metoclopramide, metolol, metoprolol, metyrosine, mexiletine, michellamine B, micronomicin, midafotel, midaxifylline, mideplanin, milacainide, milnacipran, mitoxantrone, moexipril, mofegiline, moxifloxacin, mureidomycins, mycestericin E, n-[3(R)-[2-piperidin-4-yl)ethyl]-2-piperidone-1-yl]acetyl-3(R)-methyl-β-alanine, nadolol, napsamycins, nardeterol, N-desmethylmilameline, nebivolol, neboglamine, nebracetam, nepicastat, neramexane, neridronate, nemifidide, nifedipine, nimodipine, nipradilol, noberastine, noberastine, nocodazole, nolomirole, norepinephrine, norfloxacin, nornicotine, nortopixantrone, nortriptyline, nuvanil, oberadilol, octreotide, olamufloxacin, olcegepant, olradipine, orbifloxacin, orienticins, oritavancin, oseltamivir, osutidine, ovothiol A, ovothiol B, oxfendazole, oxibendazole, oxmetidine, oxolide, oxprenolol, pafenolol, palau'amine, palindore, pamatolol, pamidronate, papuamide A, papuamide B, parbendazole, parodilol, paromomycin, paroxetine, paroxetine, pasireotide, pazufloxacin, pelagiomicin C, penbutolol, perindopril, phendioxan, phospholine, picumeterol, pindolol, p-iodorubidazone, pipedimic acid, pirbuterol, pixantrone, pluraflavin A, pluraflavin B, poststatin, practolol, pradimicin, pradimicin B, pradimicin D, pradimicin E, pradimicin FA-2, pradofloxacin, pramipexole, pranidipine, prazosin, pregabalin, premafloxacin, prenalterol, primidolol, prisotinol, prizidilol, procainamide, procaterol, propafenone, propanolol, protriptyline, proxodolol, pseudoephedrine, pyloricidin B, pyridazomycin, quinapril, quinterenol, R-(+)-aminoindan, ralfinamide, ramipril, ramoplanins, ranitidine, rasagiline, ravidomycin, reboxetine, remacemide, repinotan, reproterol, restricticin, rhodopeptins rilmazafone, rimiterol, risotilide, ritodrine, ruboxyl, sabarubicin, safinamide, safingol, salbostatin, salbutamol, salmeterol, sampatrilat, sarizotan, seglitide, seproxetine, seraspenide, sertraline, setazindol, sezolamide, sibanomicin, sibenadet, silodosin, sitafloxacin, sacoromycin, solabegron, solpecainol, soterenol, sparfloxacin, sperabillins, spinorphin, spisulosine, squalamine, styloguanidine, sulfinalol, sulfonterol, suloctidil, sulphazocine, sulphostin, sumanirole, tabilautide, tabimorelin, tafenoquine, tageflar, tolamolol, talibegron, tamsulosin, targinine, tazolol, tecalcet, telavancin, temocapril, terbutaline, tertatolol, tetrafibricin, tetrahydrazoline, tetrindol, theprubicin, thiabendazole, thiofedrine, thrazarine, tiamdipine, tiamenidine, tianeptine, tienoxolol, tigecycline, tilisolol, timolol, tinazoline, tiotidine, tipifarnib, tiprenolol, tipropidil, tirofiban, tocainide, tolazoline, tomoxetine, topixantrone, tosufloxacin, tramazoline, trandolapril, tranexamic acid, tranylcypromine, triamterene, trovafloxacin, troxipide, tuftsin, tulathromycin B, tulobuterol, ubistatin, ulifloxacin, utibapril, vestipitant, vicenistatin, vigabatrin, vildagliptin, viloxazine, vofopitant, voglibose, xamoterol, ximelagatran, xylometazoline, zabiciprilat, zelandopam, ziconotide, zilpaterol, zorubicin, α-methyltryptophan, α-methylepinephrine, (−)-cicloprolol, (−)-nebivolol, (+)-isamoltan, (+)-sotalol, (R)-(+)-amlodipine, (S)-noremopamil, 1-ethyl-6-fluoro-1,21-aminoepothilone B,4-dihydro-4-oxo-7-(1-piperazinyl)-1,4-dihydro-4-oxo-7-(piperazinyl)-3-quinolinecarboxylic acid 7-oxostaurosporine, 8-napthyridine-3-carboxylic acid, and 1-cyclopropyl-6-fluoro-1.

13. The method of claim 12, wherein the drug is chosen from R-baclofen and pregabalin.

14. The method of claim 12, wherein the drug is R-baclofen, $R^1$ is isopropyl, $R^2$ is isopropyl, $R^3$ is methyl, the enzyme is *Candida antarctica* lipase A, and the compound of Formula (III) is (3R)-4-{[(1S)-2-methyl-1-(2-methylpropanoyloxy)propoxy]carbonylamino}-3-(4-chorophenyl)butanoic acid:

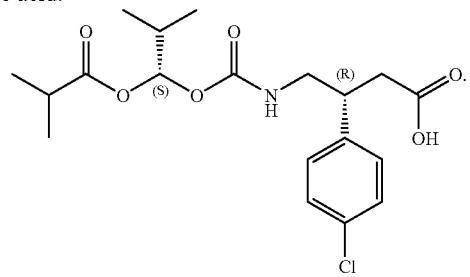

15. The method of claim 12, wherein the drug is S-pregabalin, $R^1$ is isopropyl, $R^2$ is methyl, $R^3$ is methyl, the enzyme is *Candida antarctica* lipase B, and the compound of Formula (III) is 3-({[(1R)-1-(2-methylpropanoyloxy)ethoxy]carbonylamino}methyl)(3S)-5-methylhexanoic acid:

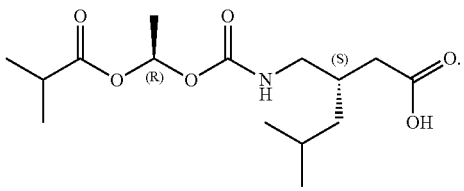

16. The method of claim 1, wherein the enantiomerically enriched mixture has an enantiomeric excess of the S isomer and the enzyme is porcine liver esterase.

* * * * *